(12) United States Patent
Sone et al.

(10) Patent No.: US 8,926,531 B2
(45) Date of Patent: Jan. 6, 2015

(54) FATIGUE ESTIMATION DEVICE AND ELECTRONIC APPARATUS HAVING THE FATIGUE ESTIMATION DEVICE MOUNTED THEREON

(75) Inventors: Motoki Sone, Kawasaki (JP); Katsuya Nakagawa, Kizugawa (JP); Yoshiharu Yamamoto, Tokyo (JP); Zbigniew Struzik, Tokyo (JP); Toru Nakamura, Tokyo (JP)

(73) Assignees: Sharp Kabushiki Kaisha, Osaka (JP); The University of Tokyo, Tokyo (JP)

( * ) Notice: Subject to any disclaimer, the term of this patent is extended or adjusted under 35 U.S.C. 154(b) by 1402 days.

(21) Appl. No.: 12/302,768

(22) PCT Filed: May 22, 2007

(86) PCT No.: PCT/JP2007/060443
§ 371 (c)(1),
(2), (4) Date: Nov. 26, 2008

(87) PCT Pub. No.: WO2007/138930
PCT Pub. Date: Dec. 6, 2007

(65) Prior Publication Data
US 2010/0137748 A1    Jun. 3, 2010

(30) Foreign Application Priority Data
May 29, 2006    (JP) .................................. 2006-148987

(51) Int. Cl.
A61B 5/11 (2006.01)
A61B 5/00 (2006.01)
G08B 21/06 (2006.01)

(52) U.S. Cl.
CPC .............. *A61B 5/1118* (2013.01); *A61B 5/681* (2013.01); *A61B 5/6887* (2013.01); *G08B 21/06* (2013.01); *A61B 5/726* (2013.01); *A61B 2562/0219* (2013.01)
USPC ........................................................ 600/595

(58) Field of Classification Search
CPC ........................................ A61B 5/1117–5/1123
USPC .................................................. 600/587, 595
See application file for complete search history.

(56) References Cited

U.S. PATENT DOCUMENTS 4,545,385 A  * 10/1985  Pirschel .......................... 600/445
4,943,986 A  *  7/1990  Barbarisi .......................... 378/37

(Continued)

FOREIGN PATENT DOCUMENTS

JP        07-178073 A      7/1995
JP        7-295715 A      11/1995

(Continued)

OTHER PUBLICATIONS

Yoshino et al. "The Effect of prolonged free-walking fatigue on gait and physiological rhythm," Journal of Biomechanics 37 (2004) 1271-1280 and in further view of Goyal et al. (US 2006/0047187 A1).*

(Continued)

*Primary Examiner* — Sean Dougherty
*Assistant Examiner* — Michael C Stout
(74) *Attorney, Agent, or Firm* — Birch, Stewart, Kolasch & Birch, LLP

(57) ABSTRACT

A body motion detection section (2) for continuously detecting the frequency of a user's activity as an activity level is provided. The activity level detected by the body motion detection section (2) is outputted to a fatigue detection section (3) for estimating a user's fatigue level on the basis of the activity level.

33 Claims, 12 Drawing Sheets

(56) References Cited

U.S. PATENT DOCUMENTS

| | | | |
|---|---|---|---|
| 5,409,497 A * | 4/1995 | Siczek et al. | 600/407 |
| 5,573,013 A * | 11/1996 | Conlan | 600/595 |
| 5,855,554 A * | 1/1999 | Schneider et al. | 600/407 |
| 6,449,508 B1 * | 9/2002 | Sheldon et al. | 607/19 |
| 6,463,319 B1 * | 10/2002 | Bucholz | 600/426 |
| 6,582,380 B2 * | 6/2003 | Kazlausky et al. | 600/595 |
| 7,171,256 B1 * | 1/2007 | Graessle et al. | 600/427 |
| 7,379,769 B2 * | 5/2008 | Piron et al. | 600/415 |
| 7,771,371 B2 * | 8/2010 | Avni | 600/592 |
| 7,828,744 B2 * | 11/2010 | Rioux et al. | 600/562 |
| 2001/0007076 A1 * | 7/2001 | Jesseph | 606/130 |
| 2001/0049470 A1 * | 12/2001 | Mault et al. | 600/300 |
| 2002/0061090 A1 * | 5/2002 | Lindstrom et al. | 378/37 |
| 2002/0156365 A1 * | 10/2002 | Tsekos | 600/411 |
| 2003/0045816 A1 * | 3/2003 | Foxlin | 600/595 |
| 2003/0139692 A1 * | 7/2003 | Barrey et al. | 600/595 |
| 2003/0233110 A1 * | 12/2003 | Jesseph | 606/167 |
| 2004/0015103 A1 * | 1/2004 | Aminian et al. | 600/595 |
| 2004/0088791 A1 * | 5/2004 | Corbeil et al. | 5/601 |
| 2004/0210159 A1 * | 10/2004 | Kibar | 600/558 |
| 2004/0215101 A1 * | 10/2004 | Rioux et al. | 600/562 |
| 2004/0228503 A1 * | 11/2004 | Cutler | 382/103 |
| 2004/0230138 A1 * | 11/2004 | Inoue et al. | 600/595 |
| 2005/0075586 A1 * | 4/2005 | Jamsen | 600/595 |
| 2005/0080333 A1 * | 4/2005 | Piron et al. | 600/417 |
| 2005/0143638 A1 * | 6/2005 | Johnson et al. | 600/407 |
| 2005/0177080 A1 * | 8/2005 | Yasuhara et al. | 602/16 |
| 2006/0047187 A1 * | 3/2006 | Goyal et al. | 600/300 |
| 2006/0058699 A1 * | 3/2006 | Vitiello et al. | 600/546 |
| 2006/0089538 A1 * | 4/2006 | Cuddihy et al. | 600/300 |
| 2006/0155175 A1 * | 7/2006 | Ogino et al. | 600/301 |
| 2006/0161079 A1 * | 7/2006 | Choi et al. | 600/595 |
| 2006/0167387 A1 * | 7/2006 | Buchholz et al. | 600/595 |
| 2006/0180379 A1 * | 8/2006 | Ferrone et al. | 180/272 |
| 2006/0270949 A1 * | 11/2006 | Mathie et al. | 600/595 |
| 2006/0282021 A1 * | 12/2006 | DeVaul et al. | 600/595 |
| 2007/0276270 A1 * | 11/2007 | Tran | 600/508 |
| 2008/0194998 A1 * | 8/2008 | Holmstrom et al. | 600/595 |
| 2009/0012388 A1 * | 1/2009 | Harter et al. | 600/422 |
| 2009/0149779 A1 * | 6/2009 | Russo et al. | 600/595 |
| 2009/0221937 A1 * | 9/2009 | Smith et al. | 600/595 |

FOREIGN PATENT DOCUMENTS

| | | |
|---|---|---|
| JP | 2005-13385 A | 1/2005 |
| JP | 2005-312868 A | 11/2005 |
| JP | 2006-271893 A | 10/2006 |
| WO | WO-02/094091 A1 | 11/2002 |
| WO | WO-2006/046648 A1 | 5/2006 |

OTHER PUBLICATIONS

Mizrahi et al. "The Influence of Fatigue on EMG and Impact Acceleration in Running," Basic Appl. Myol. 7 (2): 111-118, 1997.*

Yoshino et al. "The Effect of prolonged free-walking fatigue on gait and physiological rhythm," Journal of Biomechanics 37 (2004) 1271-1280.*

Takenoshita et al. "Development of a Portable Acceleration Monitor Device and its clinical application for the Quantitative Gait Assessment of the Elderly" Engineering in Medicine and Biology 27 Annual Conference Shanghi, China, Sep. 1-4, 2005.*

Mathie et al. "Detection of daily physical activities using a triaxial accelerometer" Medical and Biological Engineering and Computing 2003, vol. 41.*

Ohashi et al., "Analyses of long-term physical activity and the application to psychiatric and psychosomatic patients", the 18th Annual Symposium on Biological and Physiological Engineering, Oct. 6, 2003, pp. 265-268.

Ohashi et al., "Decreased Fractal Correlation in Diurnal Physical Activity in Chronic Fatigue Syndrome", Methods of Information in Medicine 43, 2004, pp. 26-29.

Nakamura et al., "Probing subjective fatigue from objective measures of locomotor activity", 47th Japanese Society Psychosomatic Medicine General Meeting, announced on May 30-31, 2006, pp. 1-2.

* cited by examiner

FIG. 6 (a)
| SAMPLE No. | 1 | 2 | 3 | 4 | 5 |
|---|---|---|---|---|---|
| SKEWNESS | −0.618 | 0.489 | 0.059 | −0.184 | −0.012 |
| AVERAGE | 0.733 | 23.372 | 27.878 | 26.394 | 28.911 |
| ACTUAL FATIGUE LEVEL | 0 | 35 | 35 | 60 | 70 |
| 50−SKEWNESS*50 | 80.896 | 25.527 | 47.037 | 59.204 | 50.592 |
| ESTIMATED FATIGUE LEVEL WITHOUT SIGMOID | −0.306 | 30.071 | 50.174 | 62.761 | 55.319 |
| ESTIMATED FATIGUE LEVEL WITH SIGMOID | 7.4792 | 26.964 | 50.217 | 65.431 | 56.61 |
FIG. 6 (b)
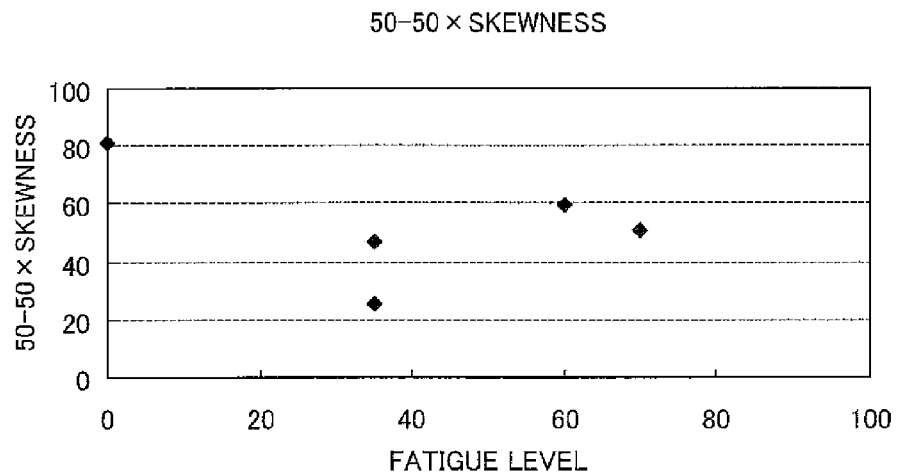
FIG. 6 (c)
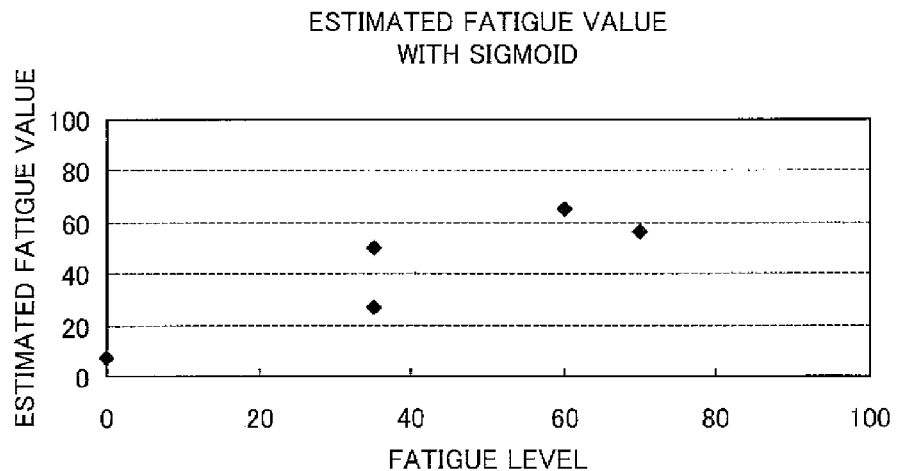

Feeling tired? How abut having a break?

You are in extreme fatigue. Please stop working and have a rest.

You seem to be tired today. You should cut your work short and take a good rest.

FATIGUE LEVEL : 62

Player ×× is feeling fatigue. You should call for the change.

Fatigue reached a peak. Now reporting to medical agency

US 8,926,531 B2

FATIGUE ESTIMATION DEVICE AND ELECTRONIC APPARATUS HAVING THE FATIGUE ESTIMATION DEVICE MOUNTED THEREON

TECHNICAL FIELD

The present invention relates to a device and method for estimating a fatigue level from a body motion of a subject.

BACKGROUND ART

Various kinds of biological information including an irregular biorhythm can be analyzed by continuously measuring a life activity. For example, Patent Document 1 discloses a technique in which information of a subject's activity can be obtained by attaching a body motion analyzing apparatus to the center of the waist in a predetermined direction. That is, in the technique disclosed in Patent Document 1, by attaching the body motion analyzing apparatus including a three-axis acceleration sensor to a waist in the predetermined direction, it is possible to detect a direction of the waist, and to distinguish whether the subject is bending down or lying. Further, in the technique disclosed in Patent Document 1, it is also possible to distinguish, from the frequency and the amplitude of AC components in an output signal of the acceleration sensor, whether the subject is walking or running.

Further, a method for estimating whether a subject is sleeping or awaking by detecting the intensity of body movement from information of the acceleration sensor attached to the subject's body has been conventionally used. Further, the most known acceleration sensor is a pedometer.

Further, physical and mental diseases can be estimated to some extent by using an apparatus for measuring a hormone in a brain and an apparatus for measuring a flow of blood. Further, body and mental disease can be estimated by conducting various tests and surveys.

For example, fatigue can be estimated by an ATMT method (Advanced Trial Making Test method). This ATMT method is a method for measuring a fatigue level based on how much time period it takes to touch numbers on a display one by one. Further, surveys are often conducted as a method for estimating physical and mental diseases including fatigue.

[Patent Document 1]
Japanese Unexamined Patent Application Publication Tokukaihei No. 7-178073 (published on Jul. 18, 1995)

DISCLOSURE OF INVENTION

However, the change of biological information caused by fatigue has not been sufficiently researched. Therefore, in the conventional art, fatigue of a subject cannot be directly detected by continuously measuring an activity of the subject. Further, in the conventional art, it is costly and complicate to detect fatigue. Therefore, fatigue cannot be detected easily.

The present invention was accomplished in view of the above problems. An object of the present invention is to provide a fatigue estimation device, a fatigue warning device, an electronic apparatus, a fatigue estimation method, a fatigue estimation program and a computer-readable storage medium, each of which enables to estimate fatigue with low cost and easily.

In order to solve the above problems, a fatigue estimation device of the present invention includes activity level detection means for continuously detecting the frequency of a user's activity as an activity level, the fatigue estimation device outputting, to fatigue level estimation means, the activity level detected by the activity level detection means, the fatigue level estimation means estimating a user's fatigue level based on the activity level.

As a result of diligent studies, the inventors of the present invention found out that there is a certain tendency in the activity level when a person feels fatigue. According to the fatigue estimation device of the present invention, a user's activity level can be automatically detected by the activity level detection means, and the fatigue level estimation means estimates a user's fatigue level on the basis of the activity level. Therefore, according to the fatigue level estimation means, a fatigue level can be automatically detected based on the activity level automatically detected by the activity level detection means.

As described above, in the fatigue estimation device of the present invention, a user's activity level is automatically detected by the activity level detection means, and a fatigue level is automatically estimated from the detected activity level by the fatigue level estimation means. Therefore, it is possible to easily estimate a user's fatigue level.

Further, a user's fatigue level can be estimated by a simple arrangement in which only the activity level detection means and the fatigue level estimation means are necessary. Therefore, it is possible to estimate a user's fatigue level with low cost.

BRIEF DESCRIPTION OF DRAWINGS

FIG. 2 (b) is a graph showing typical body motion data obtained when a person feels fatigue.

FIG. 2 (c) is a graph showing body motion data of a patient with chronic fatigue syndrome.

FIG. 2 (d) is a graph showing a difference of the body motion shown in FIG. 2 (c).

FIG. 3 (b) is a graph showing typical body motion data obtained when a person does not feel fatigue.

FIG. 3 (c) is a graph showing typical body motion data obtained when a person does not feel fatigue.

FIG. 3 (d) is a graph showing body motion data obtained by removing a trend from the body motion data shown in FIG. 3 (c).

FIG. 4 (b) is a drawing showing a state in which a person stands still when feeling fatigue.

FIG. 4 (c) is a drawing showing a state in which a person moves freely.

FIG. 4 (d) is a drawing showing a state in which a person moves freely.

FIG. 6 (a) is a table in which five samples are compared regarding the skewness and average of body motion data and a fatigue level.

FIG. 6 (b) is a drawing showing correlation between an estimated fatigue level and a value obtained by quantifying an actual fatigue level obtained as a result of a survey.

FIG. 6 (c) is a drawing showing correlation between an output value obtained by inputting an estimated fatigue level into a sigmoid function and a value obtained by quantifying an actual fatigue level.

FIG. 8 (b) is a drawing showing an output obtained by causing a vector sum of a three-axis output to pass through a high-pass filter.

FIG. 9 (b) is a flowchart showing a concrete process for calculating a fatigue level.

FIG. 10 (b) is a drawing showing an example of an appearance of a mobile phone including a fatigue warning device of the present invention.

FIG. 10 (c) is a drawing showing an example of an appearance of a mobile phone including a fatigue warning device of the present invention.

FIG. 11 (b) is a drawing showing an image of the present invention product being used in a usual manner.

FIG. 12 (b) is a drawing showing a warning message displayed on a mobile phone including a fatigue warning device of the present invention.

FIG. 12 (c) is a drawing showing a warning message displayed on a mobile phone including a fatigue warning device of the present invention.

FIG. 12 (d) is a drawing showing a warning message displayed on a mobile phone including a fatigue warning device of the present invention.

FIG. 12 (e) is a drawing showing a warning message displayed on a mobile phone including a fatigue warning device of the present invention.

FIG. 12 (f) is a drawing showing a warning message displayed on a mobile phone including a fatigue warning device of the present invention.

EXPLANATION OF REFERENCE NUMERALS

Figure 1:
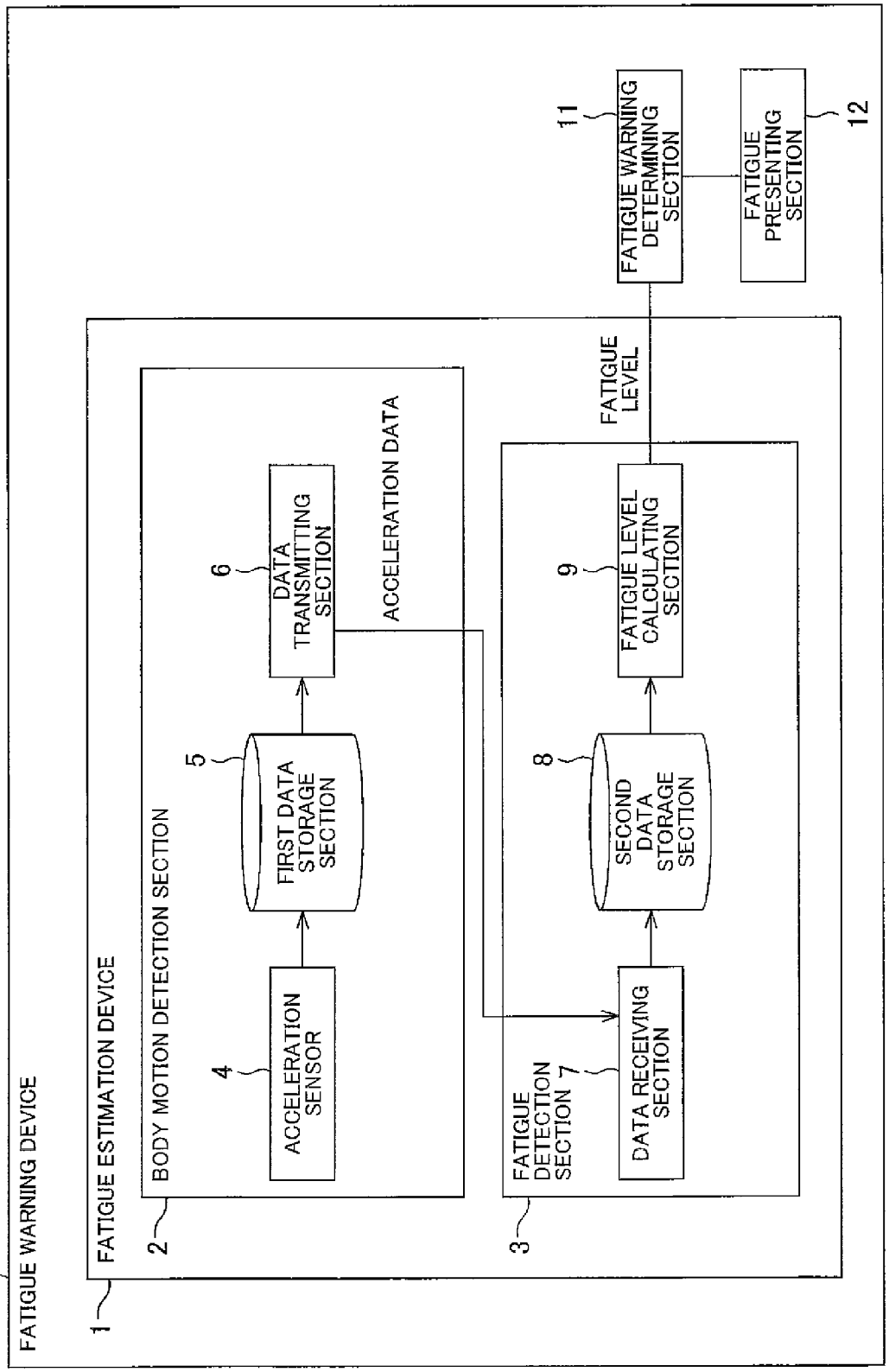
FIG. 1 is a block diagram showing an arrangement of an embodiment of the present invention.

1: Fatigue estimation device
2: Body motion detection section (activity level detection means)
3: Fatigue detection section (fatigue level estimation means)
4: Acceleration sensor (activity level detection means)
5: First data storage section (activity level detection means)
6: Data transmitting section (activity level detection means)
7: Data receiving section (fatigue level estimation means)
8: Second data storage section (fatigue level estimation means)
9: Fatigue level calculating section (fatigue level estimation means)
10: Fatigue warning device
11: Fatigue warning determining section (fatigue warning determining means)
12: Fatigue presenting section (fatigue presenting means)
201: Mobile phone including the present invention product
202: Body
203: Lid body
203a: Display section
204: Wristwatch

BEST MODE FOR CARRYING OUT THE INVENTION

[1. Change of Activity in a Fatigue State]

Explained first is a change of a person's activity in a fatigue state. A person who is feeling fatigue tries to reduce his movement. However, in many cases, the person cannot stop the activity, because a situation around him does not allow him to stop or he does not wish to stop. Therefore, even when a person continues an activity in a fatigue state, it is possible to observe a phenomenon that the person unconsciously reduces his movements.

Further, the phenomenon that a person reduces his movements in a fatigue state occurs in every part of a body. However, the reduction of movements in a fatigue state can be obtained effectively from a wrist. Especially, by counting the number of times a wrist moves for a certain time, the reduction of movements in a fatigue state can be efficiently obtained with a small number of data.

The reduction of movements in a fatigue state cannot be clearly observed just by looking at the movements equally. However, as a result of diligent studies, by closely analyzing movements of a person, the inventors found out that movements of a person in a fatigue state is different from that of non-fatigue state.

Figure 2:
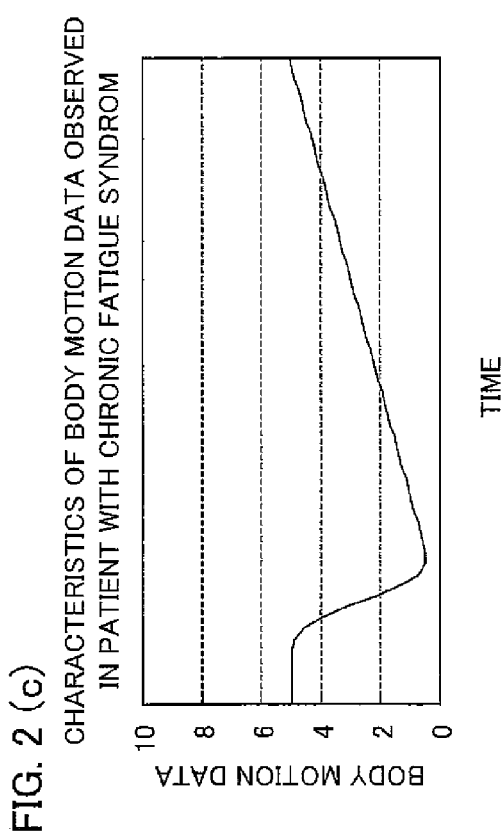
FIG. 2 (a) is a graph showing typical body motion data obtained when a person feels fatigue.
Figure 2:
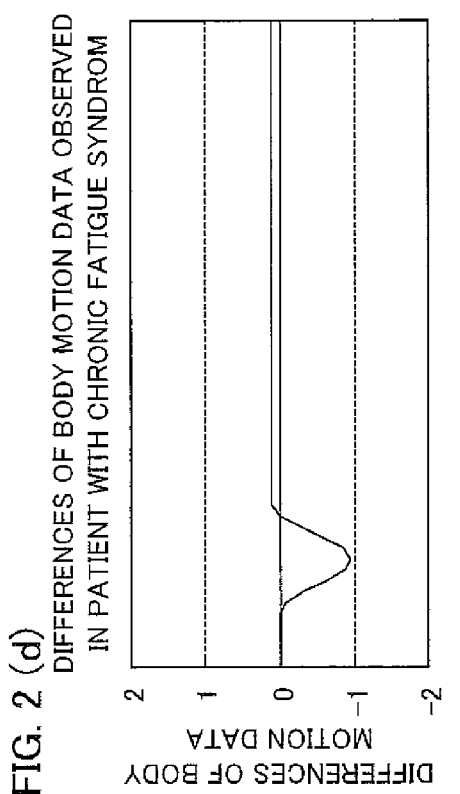
Figure 2:
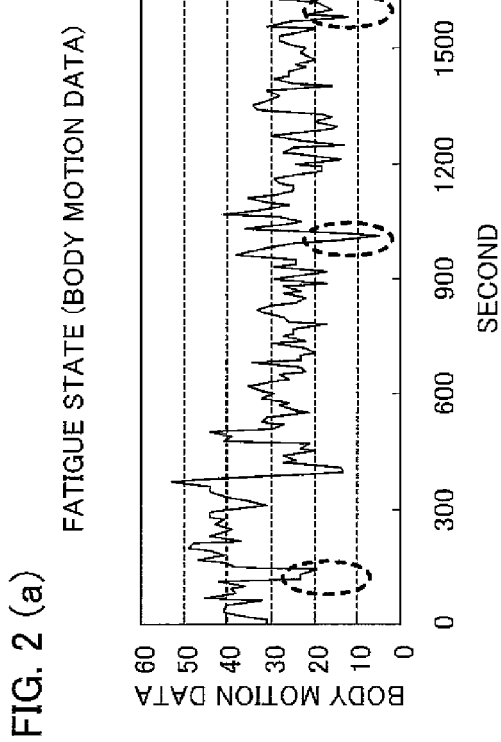
Figure 2:
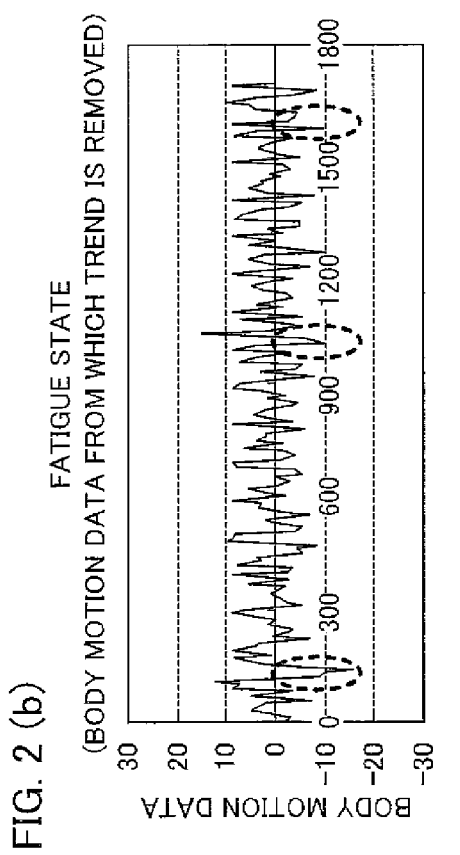
Figure 3:
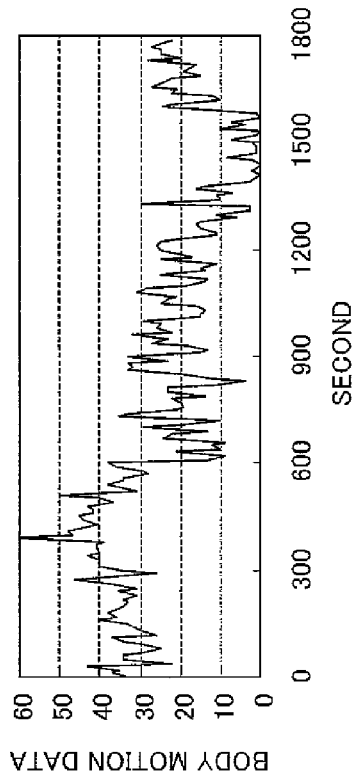
FIG. 3 (a) is a graph showing typical body motion data obtained when a person does not feel fatigue.
Figure 3:
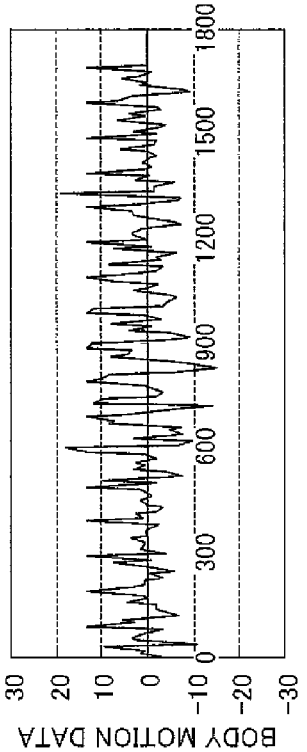
Figure 3:
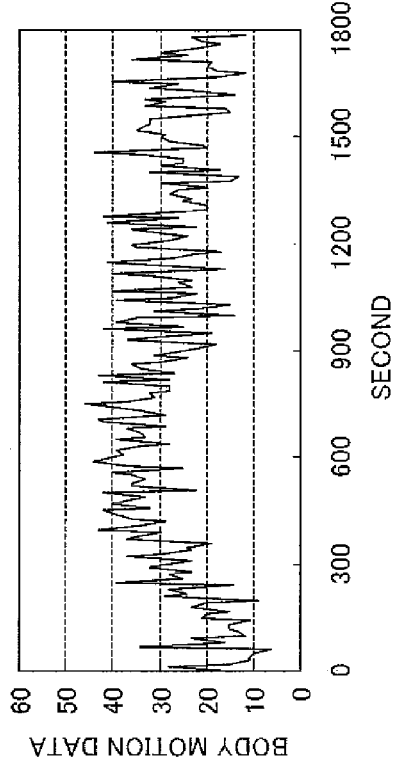
Figure 3:
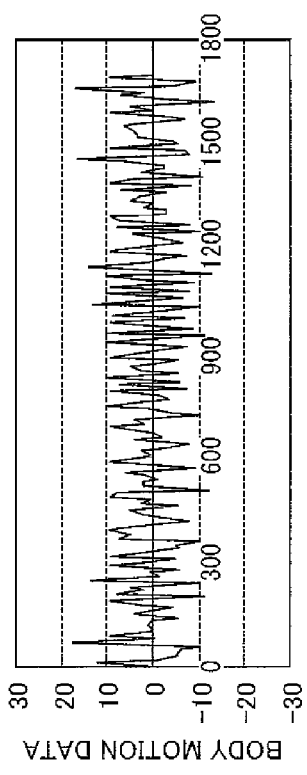
Figure 4:
FIG. 4 (a) is a drawing showing a state in which a person moves slightly when awaking.
Figure 4:
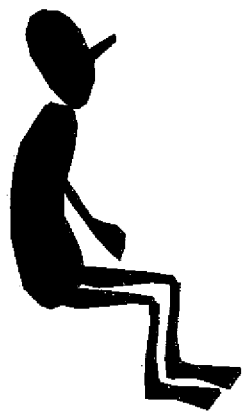
Figure 4:
Figure 4:
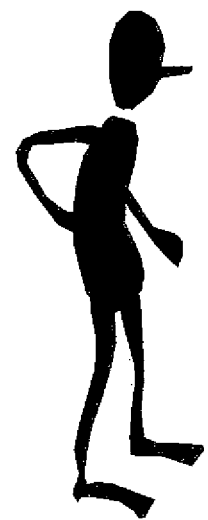

The following specifically explains the reduction of movements in a fatigue state with reference to FIGS. 2 through 4.

FIGS. 2 (a) and 2 (b) show typical body motion data obtained when a person feels fatigue, and FIGS. 3 (a) through 3 (c) show typical body motion data obtained when a person does not feel fatigue. In FIGS. 2 (a) and 2 (b) and FIGS. 3 (a) through 3 (c), a horizontal axis shows elapsed time, and a vertical axis shows body motion data obtained from an acceleration sensor attached to a wrist.

The body motion data is data obtained by quantifying the frequency of a person's activity (activity level), and a specific method for measuring the body motion data is described later. As for the vertical axis of these graphs, as the value becomes larger, the body motion data becomes higher, and as the value becomes smaller, the body motion data becomes lower. Further, if the value of the body motion data is 0, a person is not moving at all. Although differing in degree, even a person taking a rest moves slightly when awaking (see FIG. 4 (a)). Therefore, the body motion data becomes high to some extent. On the other hand, a person hardly moves when sleeping. Therefore, the body motion data approaches 0.

As a result of diligent studies, the inventors of the present invention found out that as shown in FIG. 2 (a), when a person is awake and is feeling fatigue, there is a tendency that relatively high body motion data is continuously obtained, and only for a short time, body motion data lower than a neighboring area (neighboring time) is obtained.

Further, as shown in FIG. 3 (a), when a person is awake and is not feeling fatigue, in many cases, there is no tendency that only for a short time, body motion data lower than a neighboring area is obtained. Alternatively, as shown in FIG. 3 (c), there is a case in which body motion data is wide ranged because only for a short time, body motion data lower than a neighboring area is obtained, and only for a short time, body motion data higher than a neighboring area is obtained.

Such tendency of body motion data can be theorized as follows.

Because a person moves more or less when awaking, body motion data in accordance with the movement is obtained. However, in a fatigue state, a person often stops his movement regardless of his will to continue the movement (see FIG. 4 (b)), and as shown in a portion encircled by a broken line circle in FIGS. 2 (a) and 2 (b), a phenomenon that only for a short time, body motion data lower than a neighboring area is obtained can be seen. This resembles a long time exercise such as marathon in which a person can successively continue the exercise at the start, but wants to rest frequently after exercising for a long time.

Further, when a person is not feeling fatigue, it is possible to continue an activity according to his will. Therefore, unlike the fatigue state, a phenomenon that only for a short time, body motion data becomes low cannot be seen. Alternatively, a person can freely move according to a situation around him (see FIGS. 4 (c) and 4 (d)). Therefore, body motion data is widely ranged.

As described above, a fatigue level is strongly reflected on body motion data. Therefore, it is possible to estimate a person's fatigue level from body motion data. More specifically, it is possible to estimate a fatigue level by detecting relatively low body motion data.

[2. Method for Estimating a Fatigue Level]

Next, a specific method for measuring a person's fatigue level on the basis of a change of an activity in a fatigue state is explained.

2-1. Method for Measuring Body Motion Data

Figure 5:
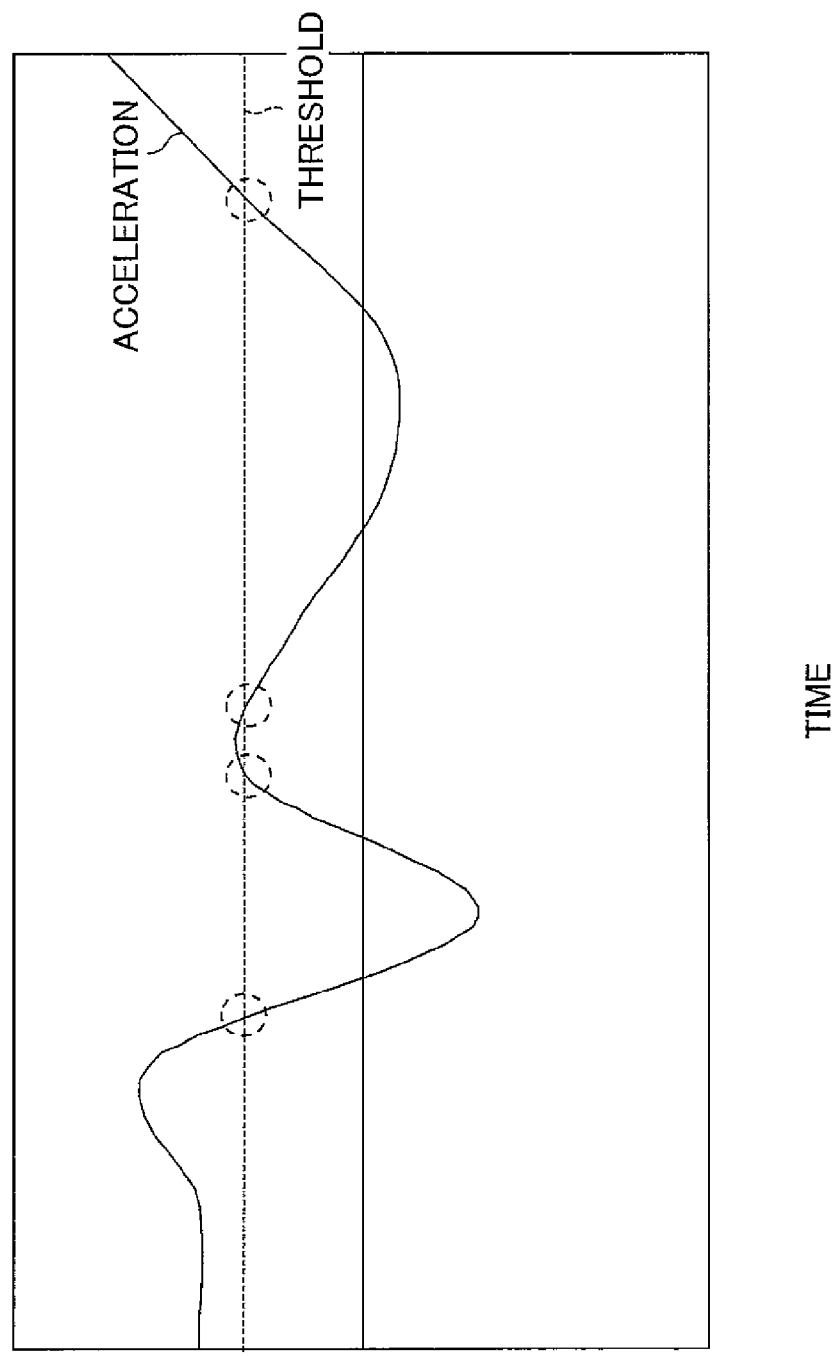
FIG. 5 is a drawing showing a data obtained by causing one-axis output to pass through a high-pass filter in order to observe a change of acceleration, the one-axis output being obtained from an acceleration sensor attached to a wrist.

First, a method for measuring body motion data is explained with reference to FIG. 5. FIG. 5 is a drawing showing a data obtained by causing one-axis output to pass through a high-pass filter in order to observe a change of acceleration, the one-axis output being obtained from an acceleration sensor attached to a wrist. By causing an output of an acceleration sensor to pass through a high-pass filter, it is possible to cancel components in the gravity direction which components appear perpetually.

The body motion data shown in FIG. 2 (a), FIG. 3 (a) and other figures is a data recording how many times the output of the acceleration sensor passed through a high-pass filter (acceleration data) in FIG. 5 passes a threshold of 0.01 G in a unit time.

For example, if the unit time is a time between a left end and a right end of the graph of FIG. 5, the output of the acceleration sensor passes a threshold four times. Therefore, it is measured that body motion data is 4. The thus measured body motion data is generally called zero crossing data and is used for analysis such as judging whether sleeping or awaking, and analyzing a biorhythm.

The data of FIG. 5 is obtained by causing the output of the acceleration sensor to pass through the high-pass filter because the change of the body motion data can be observed effectively. However, the output of the acceleration sensor does not necessarily need to pass through the high-pass filter. For example, the change of the body motion data can be observed effectively by subtracting the moving average value concerning the output value of the acceleration sensor from the output value of the acceleration sensor itself.

Further, a fatigue level can be estimated without measuring the zero crossing data. When body motion data is calculated from a vector sum of a three-axis output obtained from an acceleration sensor, it is possible to obtain more accurate body motion data with no axial bias.

Sufficiently accurate body motion data can be obtained even by calculating body motion data from a one-axis output of an acceleration sensor. This makes it possible to estimate a fatigue level with low cost and without the need for complicated calculation. Therefore, in the present embodiment, an embodiment in which body motion data is obtained from a one-axis output of an acceleration sensor is mainly explained.

[2-2. Method for Calculating a Fatigue Level]

A difference of a person's activity shown by the body motion data shown in FIGS. 2 (a), 3 (a) and 3 (c) can be estimated by a method explained below.

First, a trend of body motion data is removed. The trend can be removed as explained below. The wording "trend" means a long-term tendency of a change of body motion data.

Specifically, a regressive curve of body motion data is obtained by dividing body motion data into smaller sections and calculating a first order approximation of the data of the respective sections by using a least squaremethod. It is possible to grasp the trend of the body motion data by the regression curve.

When $x(t_i)$ is a value shown by the body motion data of FIGS. 2 (a), 3 (a) and 3 (c) and $x_{tr}(t_i)$ is a value of the body motion data in the regressive curve, $y(t_i)$ which is body motion data from which the trend is removed can be expressed as follows:

$$y(t_i)=x(t_i)-x_{tr}(t_i)$$

where $t_i$ is time at which data is obtained.

When the trend is removed in this way, the body motion data shown in FIG. 2 (b) can be obtained from the body motion data shown in FIG. 2 (a), the body motion data shown in FIG. 3 (b) can be obtained from the body motion data shown in FIG. 3 (a), and the body motion data shown in FIG. 3 (d) can be obtained from the body motion data shown in FIG. 3 (c).

When the trend is removed, a change of body motion data becomes more remarkable. Further, the change of body motion data can be clearly observed by calculating the skewness of body motion data from the following formula:

$$\text{Skew} = \frac{n}{(n-1)(n-2)} \sum_{i=1}^{n} \left(\frac{y(t_i) - \mu}{s}\right)^3$$

For example, in a fatigue state, the skewness of body motion data from which the trend is removed is −0.0118, but in a non-fatigue state, the skewness of body motion data from which the trend is removed becomes larger and is a positive value. That is, the skewness is strongly related to fatigue.

When the skewness is small, the number of data which is remarkably small is more than the data which is remarkably large. That is, when a fatigue level is high, the skewness becomes small. This coincides with the tendency of fatigue shown by the body motion data of FIGS. 2 (a), 3 (a) and 3 (c).

FIG. 6 (a) is a table in which five samples are compared regarding the skewness and the average of body motion data, and a fatigue level. It should be noted that the "actual fatigue level" shown in FIG. 6 (a) is information obtained by quantifying a fatigue level obtained as a result of a survey, and can be termed as actual fatigue level information.

Further, when a fatigue level (Fatigue) is calculated directly from the skewness (Skew) by using the following formula, a moderate tendency can be obtained:

$$\text{Fatigue}=50-50\times\text{Skew}$$

FIG. 6 (*b*) shows correlation between an estimated fatigue level by using the above formula and a value obtained by quantifying an actual fatigue level obtained as a result of a survey. Further, FIG. 6 (*c*) shows correlation between an output value obtained by inputting an estimated fatigue level into a sigmoid function and a value obtained by quantifying an actual fatigue level.

By reference to FIGS. 6 (*b*) and 6 (*c*), it is clear that as for four samples among five samples, there is a good correlation between the fatigue level estimated by using the formula and the actual fatigue level. On the other hand, it is clear that as for one sample, there is no good correlation.

There is a case in which it is not possible to accurately estimate a fatigue level when the fatigue level is estimated by using the formula Fatigue=50−50×Skew. This is because the influence on the skewness differs according to the average value of body motion data. The average value of body motion data is the most important factor next to the skewness.

Therefore, it is possible to more accurately estimate a fatigue level by using, for example, the following formula:

Fatigue=0.732×Mean+58.321×Skew−4.028×Mean× Skew+33.370 where the "Mean" is the average value of body motion data, and the "Skew" is the skewness of body motion data from which the trend is removed.

When fatigue is estimated only from the skewness, it is possible to estimate a fatigue level by using a simple formula and therefore it is possible to estimate with low burden. However, by combining a statistical analysis method, it is possible to accurately estimate a fatigue level. Further, the statistical analysis method is not limited to a method using the average and the skewness.

For example, as described below, by using the standard deviation and the kurtosis of body motion data, it is possible to more accurately estimate a fatigue level:

$$\text{Fatigue} = 3.436 \times \text{mean} + 16.392 \times sd +$$
$$(-62.426) \times \text{skew} + 4.409 \times \text{kurtosis} + (-0.615) \times \text{mean} \times sd +$$
$$1.199 \times \text{mean} \times \text{skew} + (-0.173) \times \text{mean} \times \text{kurtosis} + (-35.000)$$

where:

mean: the average value of the Zero Crossing Data of last 30 minutes sd: the standard deviation of the Zero Crossing Data of last 30 minutes from which the trend is removed skew: the skewness of the Zero Crossing Data of last 30 minutes from which the trend is removed kurtosis: the kurtosis of the Zero Crossing Data of last 30 minutes from which the trend is removed Further, coefficients and statistical values used in the above formula are merely examples, and it is needless to say that the coefficients and the statistical values may be different according to a measuring device to be used, a person to be examined and a portion of a body to be measured.

Further, it is unnecessary to use uninterrupted body motion data in estimating fatigue, and body motion data may be interrupted to some extent.

[2-3. Tendency of Body Motion Data of a Patient with Chronic Fatigue Syndrome]

Further, FIG. 2 (*c*) is a drawing showing body motion data of a patient with chronic fatigue syndrome. As a result of diligent studies, the inventors of the present invention found out that as shown in FIG. 2 (*c*), in the body motion data of a patient with chronic fatigue syndrome, the graph falls more rapidly and rises more slowly than that of an ordinary person.

Here, FIG. 2 (*d*) is a graph showing a difference from the body motion data shown in FIG. 2 (*c*), and shows a data obtained by removing a long-term fluctuation component of the body motion data shown in FIG. 2 (*c*). As shown in FIG. 2 (*d*), in a part where the body motion data falls rapidly, a difference value becomes a negative value for a short time, and in a part where the body motion data rises slowly, a difference value becomes a small positive value for a long time. Such a characteristic of body motion data can be grasped by statistically analyzing a difference value of the body motion data. For example, when body motion data falls rapidly and rises slowly, the skewness of the body motion data becomes small.

Although the body motion data shown in FIG. 2 (*a*) and the body motion data shown in FIG. 2 (*c*) are different from each other at first sight, both of them bear the characteristic of the body motion in a fatigue state because a similar characteristic can be seen by removing a difference.

The fluctuation of body motion data caused by fatigue (fluctuation based on a relatively low activity state) explained above can be grasped by a method except the statistical method. For example, it is possible to use a method (WTMM method: Wavelet Transform Modulus Maxima) in which characteristic waveforms are observed by performing a wavelet analysis which is one of a frequency analysis.

[2-4. Adjustment Process of an Estimated Fatigue Level]

A fatigue level can be estimated by using the above formulas. However, when the above formulas are used, there is a case in which the minimum value of the estimated fatigue level is less than 0 and the maximum value is more than 100. For example, in one sample among the five samples shown in FIG. 6 (*a*), when an actual fatigue level is 0, an estimated fatigue level becomes −0.306, that is, less than 0.

In such a case, it may be difficult to estimate a fatigue level. Therefore, when a fatigue level is estimated, an adjustment process is carried out so that the fatigue level is within a predetermined range (0 through 100 in the present embodiment).

Further, it is possible to clearly observe a fluctuation of a user's fatigue level by using a function having a high sensitivity in the vicinity of a specific value (e.g. in the vicinity of 50). A method using an output of a sigmoid function can be appropriately used in such a process. An example of the sigmoid function is shown below.

$$F(x) = \frac{100}{1 + \exp(-0.05 \times (x - 50))}$$

Figure 7:
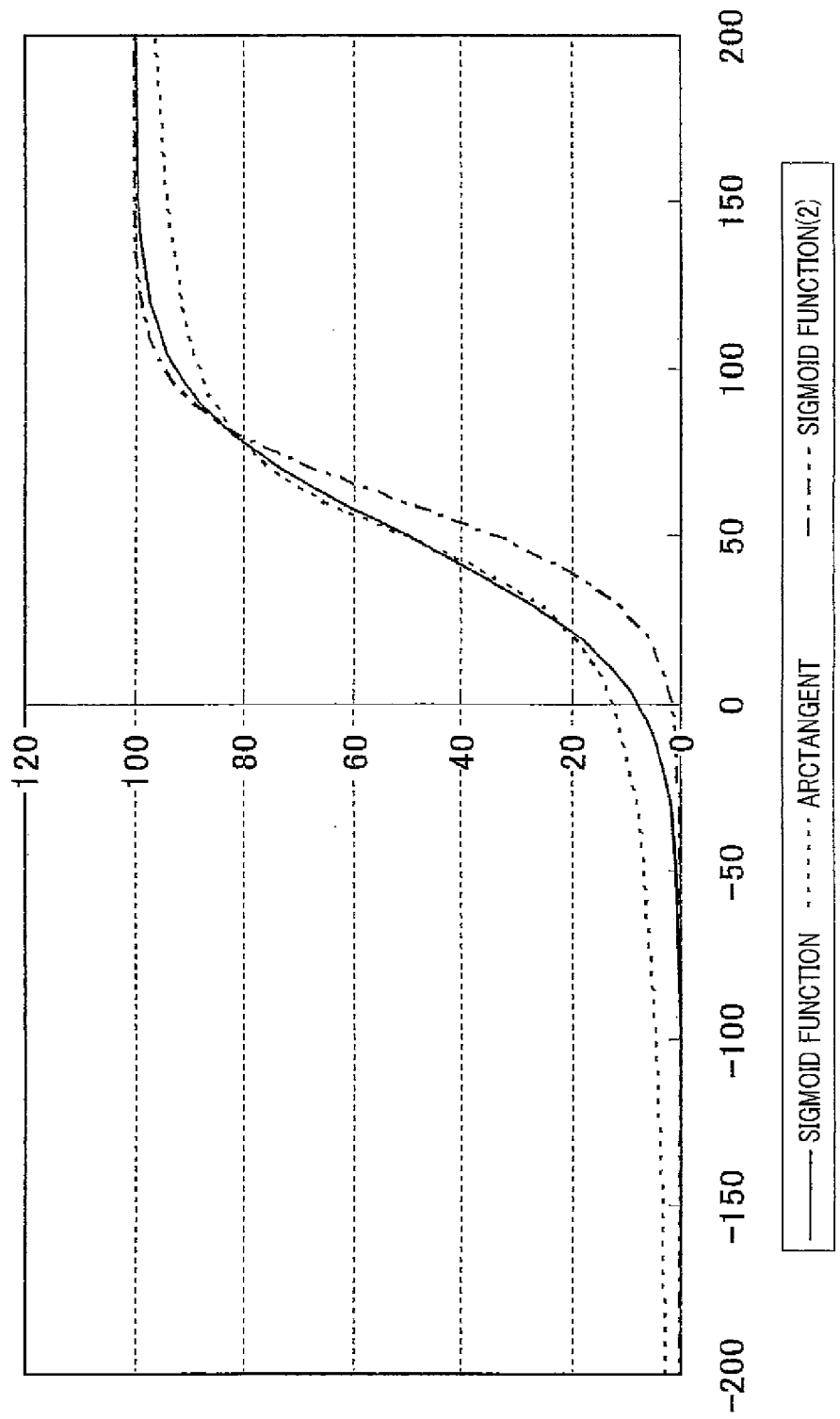
FIG. 7 is a drawing showing a sigmoid function and an arctangent function.

As shown by the solid line of FIG. 7, in the sigmoid function, a slope of the function is approximately 1 in the vicinity of 50, and as further from 50, the slope becomes more gradual, and the line does not exceed the range of 0 through 100.

As described above, the sigmoid function has the steepest slope in the vicinity of 50 and is most sensitive. Therefore, it is possible to clarify a subtle change of a characteristic in the vicinity of 50. Furthermore, the slope of the function is always positive. Therefore, a change between a positive value and a negative value is not caused.

By using the sigmoid function having such a characteristic, it is possible to adjust the fatigue level of −0.306 described above into a positive value close to 0, that is, 7.48. As shown in FIG. 6 (*a*), by using the sigmoid function, fatigue levels of 30.07 and 50.17 can be similarly adjusted into 26.96 and 50.22, respectively. Further, a difference between the adjusted value and the value before the adjustment is small.

There are innumerable functions which have the same characteristic as the sigmoid function, and the function should be selected according to the use. An exemplary function except the sigmoid function is the arctangent function which is shown by the broken line in FIG. 7. When the sigmoid function shown in FIG. 7 is used, a value of not less than 100 and a value of not more than 0 approach 100 and 0 to a large extent, respectively. However, even if a fatigue level is not less than 100 or not more than, a difference of the fatigue level can be more clarified by using the arctangent function.

Further, although the method for heightening the sensitivity in the vicinity of 50 was explained, a part in which the sensitivity is heightened is not limited to the vicinity of 50 and may be changed according to the use.

For example, the one-dot chain line in FIG. 7 represents a sigmoid function described below. According to this sigmoid function, it is possible to heighten the sensitivity in the vicinity of 80 through 90.

$$F(x) = \frac{100}{1+\exp(-0.07 \times (x-60))}$$

Further, if calculation becomes complicated by using such a filter (sigmoid function, arctangent function and the like), a value of not more than 0 may be set to be 0 and a value of not less than 100 may be set to be 100 without exception.

2-5. Example of Body Motion Data

It is unnecessary to limit body motion data used for estimation of a fatigue level to the zero crossing data, and the threshold may be more than one. For example, as a different data from the zero crossing data, an output data (acceleration data) from an acceleration sensor shown in FIGS. 8 (a) and 8 (b) may be used.

Figure 8:
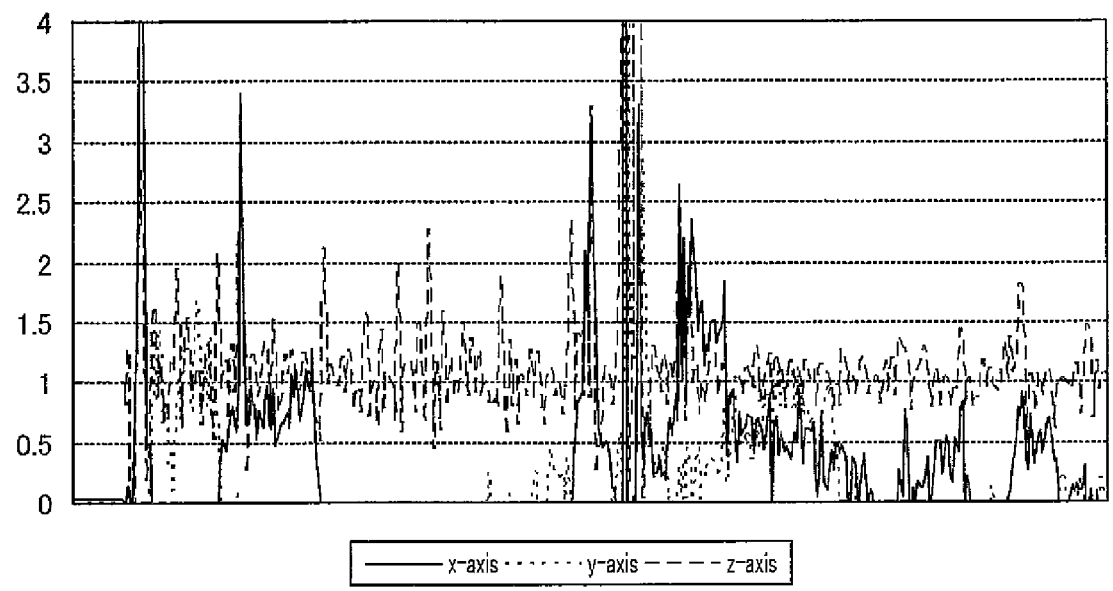
FIG. 8 (a) is a drawing showing a result obtained by measuring, for a certain time, a three-axis output from an acceleration sensor attached to a wrist.
Figure 8:
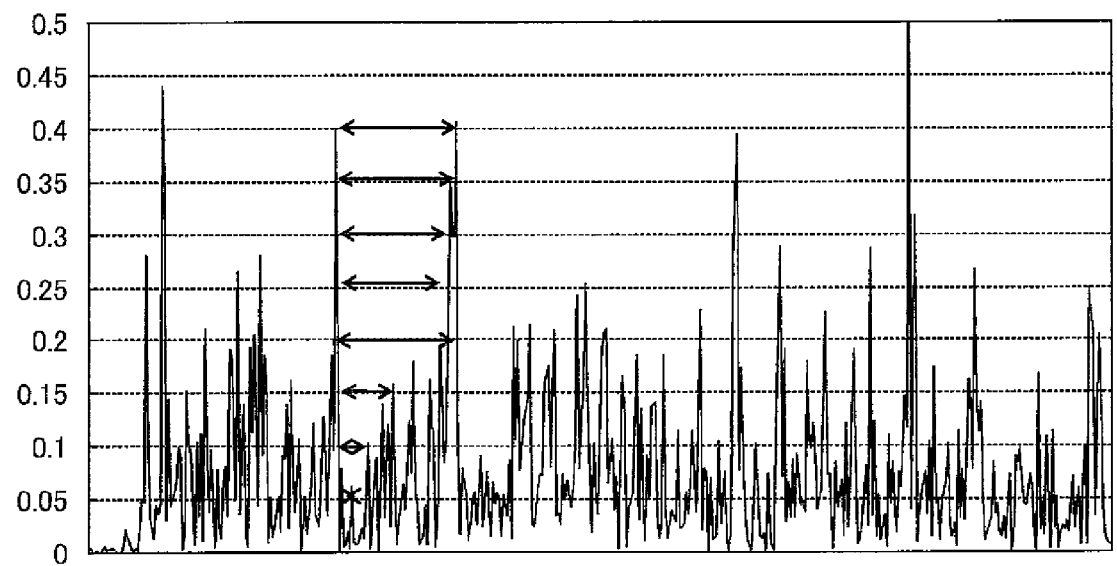

FIG. 8 (a) is a drawing showing a result obtained by measuring a three-axis output from an acceleration sensor attached to a wrist for a certain time. The vertical axis shows an acceleration whose unit is 1 G. If there is no movement, a vector sum of a three-axis output becomes 1 G which is the same as the acceleration of gravity.

FIG. 8 (b) is a drawing showing an output obtained by causing the vector sum of the three-axis output to pass through a high-pass filter. If there is no movement, the acceleration data shown in FIG. 8 (b) is constantly 0. However, a value except 0 is outputted according to movements of the wrist.

The estimation of the fatigue level by using the acceleration data shown in FIGS. 8 (a) and 8 (b) can be realized by adopting the following method. That is, for example, a plurality of thresholds are provided at 0.05 G intervals in the acceleration data shown in FIGS. 8 (a) and 8 (b). For each of the thresholds, an elapsed time (part designated by the arrow) between a time at which the acceleration data changes from a value higher than the threshold to a value lower than the threshold and a time at which the acceleration data changes from a value lower than the threshold to a value higher than the threshold is calculated. For example, the average and the variance are analyzed as amount of statistics of this elapsed time.

When a person moves actively, the average of the elapsed time for a high threshold becomes shorter and the variance becomes smaller. On the other hand, when a person does not move actively, the elapsed time for a high threshold tends to become longer and the variance becomes larger.

Therefore, in a fatigue state as shown in FIG. 2, the output of the acceleration sensor more often exceeds a high threshold, and the average of the elapsed time becomes shorter. Further, because the output of the acceleration sensor becomes lower than the neighboring area for a short time, the variance becomes larger. By conducting a similar analysis on each threshold provided in the output of the acceleration sensor, it is possible to more accurately find a fatigue level.

[2-6. Summary]

As described above, whether a subject is feeling fatigue or not changes the activity status, and the change can be seen in how relatively low body motion data appears in body motion data continuously measured. A method for discerning the change of the body motion data is not limited to a statistical method, and a method for evaluating a fractal such as a DFA (Detrend Fluctiation Analysis) and a WTMM (Wavelet Transform Modulus Maxima) can be used. There is a case in which body motion data can be more accurately discerned by using these methods. However, when these methods are used, an amount of calculation increases. Therefore, when a fatigue level is evaluated by using a mobile apparatus or the like, a method for estimating a fatigue level from about two statistical values (e.g. average and skewness) is the best method judging from the accuracy and the amount of calculation. Therefore, the following explains a fatigue warning device having a function of estimating a fatigue level by using two statistical values of the average and the skewness.

[3. Arrangement of a Device]

First, an arrangement according to an embodiment of a fatigue estimation device of the present invention is explained with reference to FIG. 1. As shown in FIG. 1, a fatigue estimation device 1 of the present embodiment includes a body motion detection section (activity level detection means) 2 and a fatigue detection section (fatigue level estimation means) 3. Further, as shown in FIG. 1, a fatigue warning device 10 of the present embodiment includes the fatigue estimation device 1, a fatigue warning determining section (fatigue warning determining means) 11 and a fatigue presenting section (fatigue presenting means) 12.

The body motion detection section 2 detects a movement of a user's body (body motion) and has a shape of a wrist watch which can be attached to the wrist. The body motion detection section 2 includes an acceleration sensor (activity level detection means) 4, a first data storage section (activity level detection means) 5 and a data transmitting section (activity level detection means) 6.

The acceleration sensor 4 senses an acceleration of the wrist, and an acceleration data obtained by the acceleration sensor 4 is stored in the first data storage section 5 for a certain time. The data stored in the first data storage section 5 is transmitted to the fatigue detection section 3 via the data transmitting section 6. Even if the transmission of the acceleration data by the data transmitting section 6 is stopped for a short time, the acceleration data is once stored in the first data storage section 5, and therefore it is possible to read, from the first data storage section 5, the acceleration data which was not transmitted and it is possible to transmit the acceleration data from the data transmitting section 6 to the fatigue detection section 3 without pause.

The fatigue detection section 3 can be realized by a portable small device and is preferably provided in a mobile phone. Further, the fatigue detection section 3 includes a data receiving section (fatigue level estimation means) 7, a second data storage section (fatigue level estimation means) 8 and a fatigue level calculating section (fatigue level estimation means) 9.

The data receiving section 7 receives an acceleration data transmitted from the data transmitting section 6 of the body motion detection section 2. The acceleration data which the data receiving section 7 received is stored in the second data storage section 8. The fatigue level calculating section 9 calculates a fatigue level (Fatigue) by using the acceleration data stored in the second data storage section 8 and the above-mentioned formulas.

The fatigue warning determining section 11 determines, on the basis of the fatigue level (Fatigue) calculated by the fatigue level calculating section 9, whether a warning should be issued or not to a user. A determining process of the fatigue warning determining section 11 is described later.

If the fatigue warning determining section 11 determined that a warning should be issued to the user, the information is sent to the fatigue presenting section 12, and as described later, a warning and a message according to a level of fatigue is given to the user.

The arrangement shown in FIG. 1 is one example for realizing the present invention, and another arrangement is possible. For example, in FIG. 1, the body motion detection section 2, the fatigue warning determining section 11 and the fatigue presenting section 12 are separately arranged. This is because the body motion detection section 2 is made compact so as not to lay a burden on the user, and the fatigue presenting section 12 is made large so as to convey a large amount of information. However, the body motion detection section 2, the fatigue warning determining section 11 and the fatigue presenting section 12 may be integral with each other.

Further, when the body motion detection section 2 and the fatigue detection section 3 are provided in the same device, the first data storage section 5, the data transmitting section 6 and the data receiving section 7 may be omitted. Further, if a data can be transmitted between the fatigue warning determining section 11 and the fatigue level calculating section 9 and between the fatigue presenting section 12 and the fatigue level calculating section 9, (i) the fatigue detection section 3 and (ii) the fatigue warning determining section 11 and the fatigue presenting section 12 can be realized in different devices. Further, another arrangement is possible in which the fatigue presenting section 12 is omitted, and a fatigue level and a degree of risk are transmitted to a medical agency and a manager of a user via network.

In the above embodiment, a fatigue level is estimated from an activity level of a part of a body (wrist). However, it is needless to say that a fatigue level can be estimated by attaching a similar sensor not only to a wrist but also to an entire body. The wrist is suitable for measurement of body motion data because the wrist is a part which a person frequently moves. However, the wrist is moved also by external factors, for example, when a person is on a vehicle. In this case, the accuracy of estimation of a fatigue level deteriorates.

For example, the wrist normally does not move during sleep, but when a person is on a vehicle, the wrist may be moved due to shaking of the vehicle. It is meaningless to estimate a fatigue level on the basis of acceleration due to the shaking. In order not to mistake shaking due to external factors for an activity level, it is preferable that by measuring acceleration of an entire body (e.g. waist, leg, trunk and head), acceleration due to shaking of a vehicle is offset by the acceleration of an entire body.

Further, when a fatigue level cannot be estimated from acceleration of the wrist, a fatigue level can be estimated from movements of the second and third candidates for acceleration measurement (e.g. waist, leg, trunk and head). For example, medical personnel need to take off wristwatches and wash their hands in order to prevent infection, and in some situations, they may not put on wristwatches for a while after that. In this case, by measuring an activity level from a body part except the wrist and by estimating a fatigue level from the activity level, fatigue can be continuously and accurately estimated.

Further, in FIG. 1, the acceleration sensor 4 is used as a sensor of the body motion detection section 2. However, in FIGS. 2, 3 and 4, the method for detecting a tendency of body motion data in a fatigue state is not limited to a method using an acceleration sensor.

For example, it is possible to detect a tendency of body motion data in a fatigue state by detecting positional information. In this case, when positional information outputted from a positional information sensor attached to a user's body is received by using a communication method such as a UWB (Ultra Wide Band), it is possible to speedily detect the user's positional information. When positional information is detected, by detecting the change of positional information in chronological order, the change of the positional information can be converted into user's speed information for each instant of time, and the change of the speed information can be converted into information on user's acceleration.

It is also theoretically possible to detect user's fatigue by using imaging means such as a video camera in acquiring image information of a user's body motion. When the image information is used, movements of a part of a subject's body (e.g. arm and head) are continuously observed by image recognition processing. Like the case in which an output of an acceleration sensor is used for estimation of a fatigue level, by differentiating twice a change amount of movements of a body part with respect to time, acceleration of the body part can be acquired. After the acceleration is acquired from the image information, a fatigue level can be estimated by a similar process as the case in which an acceleration sensor is used.

The use of a camera has an advantage because a user's body motion can be grasped without restricting user's actions. However, the user is required to be always near the camera, and there is a case in which enormous amounts of calculation is needed in order to acquire body motion data from image information. Further, by using the UWB, it is possible to speedily acquire image information of a user's body motion and to efficiently estimate a fatigue level.

In the fatigue estimation device 1 of the present embodiment, body motion data is measured by the acceleration sensor 4 because a fatigue level can be more accurately and easily estimated by using the acceleration sensor 4.

[4. Processing Flow]

Figure 9:
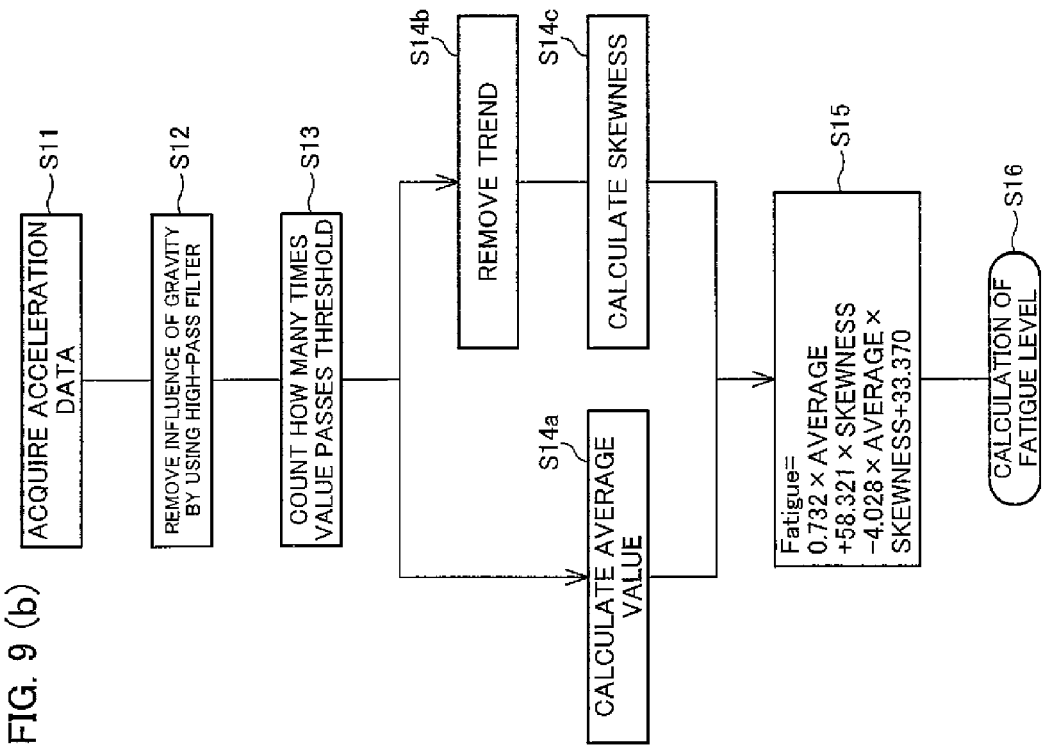
FIG. 9 (a) is a flowchart showing an embodiment of a fatigue estimation method of the present invention.
Figure 9:
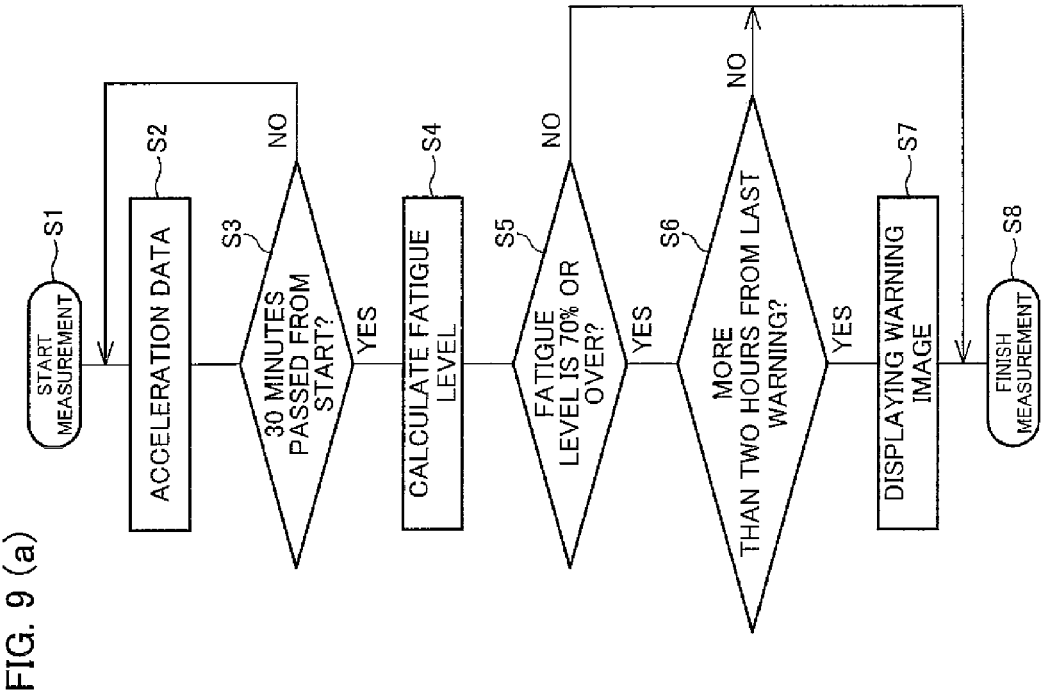

FIG. 9 (a) is a flowchart of a fatigue estimation method realized by the fatigue estimation device 1 or the fatigue warning device 10.

First, the acceleration sensor 4 starts measurement of an acceleration data (S1). Then, the acceleration sensor 4 continuously acquires the acceleration data (S2) and at the same time judges whether or not a predetermined time (e.g. 30 minutes) has passed from the start of the measurement. Thus, the acceleration data measured by the acceleration sensor 4 until the predetermined time passes from the start of the measurement is stored in the first data storage section 5.

As described above, the acceleration data stored in the first data storage section 5 is stored in the second data storage section 8 via the data transmitting section 6 and the data receiving section 7. The fatigue level calculating section 9 calculates a fatigue level from the acceleration data stored in the second data storage section 8 by using the above-mentioned formulas (S4).

FIG. 9 (*b*) shows a processing flow for calculation of a fatigue level. First, the fatigue level calculating section 9 acquires the acceleration data stored in the second data storage section 8 (S11) and removes the influence due to the gravity from the acceleration data by using a high-pass filter (S12).

The fatigue level calculating section 9 counts how many times the acceleration data from which the influence due to the gravity is removed passes a predetermined threshold (S13) and thereby acquires zero crossing data, that is, body motion data.

Then, the fatigue level calculating section 9, at the same time, calculates an average value (Mean) of the body motion data (S14*a*), removes the trend from the body motion data (S14*b*) and calculates the skewness (Skew) of the body motion data (S14*c*).

The fatigue level calculating section 9 calculates a fatigue level (Fatigue) from the average value (Mean) calculated at the S14*a* and the skewness (Skew) calculated at the S14*c* by using the following formula (S15).

$$\text{Fatigue}=0.732\times\text{Mean}+58.321\times\text{Skew}-4.028\times\text{Mean}\times\text{Skew}+33.370$$

Calculation of the fatigue level (Fatigue) is completed by carrying out the above steps (S16).

The fatigue warning determining section 11 judges whether or not the calculated fatigue level (Fatigue) is not less than a predetermined value (e.g. 70%) (S5) and judges whether or not a predetermined time (e.g. two hours) has passed since the last warning was issued (S6). Here, the "warning" means that information that a user is feeling fatigue is delivered to the user and people involved through screen display or by other means. The detailed explanation of the "warning" is described later.

When the fatigue warning determining section 11 judges "Yes" at both of the S5 and S6, the fatigue presenting section 12 displays on a predetermined screen a warning that the user is feeling fatigue (S7). Further, when the fatigue warning determining section 11 judges "No" at one of the S5 and S6, the fatigue presenting section 12 does not display the warning.

When the warning displayed in the screen at the S7 disappears, the acceleration sensor 4 completes the measurement of the acceleration data (S8).

By following the flow explained above, it becomes impossible to carry out next estimation of the fatigue level until the acceleration data necessary for the estimation of the fatigue level is stored in the second data storage section 8. However, by using the acceleration data stored in the second data storage section 8 in the past, it is possible to estimate a fatigue level at any point of time to some extent.

Further, when a fatigue level is estimated at shorter intervals than a time necessary for accurate estimation of a fatigue level, the fatigue level may be outputted according to the request of the user. However, the number of the fatigue level which the user refers to becomes larger, and the fatigue levels are similar to each other. Therefore, there is a case in which the user cannot have correct understanding of whether fatigue is increasing or decreasing.

Therefore, in the present embodiment, a warning is not issued until a predetermined time (two hours) passes from the previous warning. This is because it is presumable that once a warning is issued, a user will take measures to reduce fatigue (take a rest etc.). Further, it is unimaginable that the user recovers from fatigue soon after taking a rest, and therefore it is meaningless to repeat the warning until the user recovers from fatigue.

Further, it is also preferable that not only a warning is issued to a user, but also the user is asked about his condition.

For example, if judged from a tendency of body motion data that a user is in a fatigue state, it is possible to link actual fatigue level information with estimated fatigue level information. The actual fatigue level information is obtained by asking a user whether he is aware of his fatigue or not, that is, whether a symptom is appearing or not, and the estimated fatigue level information shows a fatigue level estimated by the fatigue level calculating section 9. This makes it possible to collect a significant data for a doctor who conducts diagnosis on the user.

Alternatively, a fatigue level can be more accurately estimated by dynamically correct a coefficient of an arithmetic expression for obtaining a fatigue level and the algorithm for estimating a fatigue level. Further, it is more preferable that the result obtained by asking a patient about degree of awareness of his symptom is linked with estimated fatigue level.

In this case, the result obtained by asking a patient can be linked with fatigue level by the following process. First, when a fatigue level is estimated intermittently or continuously, the estimated fatigue level is stored in the second data storage section 8 along with corresponding time information.

Next, when the fatigue warning determining section 11 detects a fatigue level more than a predetermined level (70%), the fatigue presenting section 12 displays an inquiry on a screen about the degree of awareness of symptoms. The user inputs the degree of awareness of his symptoms by using an operation input section (not shown) of the fatigue warning device 10, and the inputted information of the degree of awareness of symptoms (actual fatigue level information) is stored in the second data storage section 8 along with corresponding time information.

By storing data as above, it is possible to link estimated fatigue level information and actual fatigue level information with respect to time.

[5. Examples of Attaching a Fatigue Estimation Device and a Fatigue Warning Device]

Next, examples of attaching a fatigue estimation device and a fatigue warning device are explained with reference to FIGS. 10 and 11.

Figure 10:
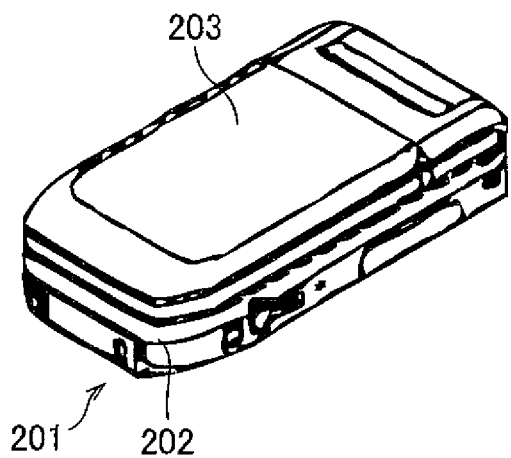
FIG. 10 (a) is a drawing showing an example of an appearance of a mobile phone including a fatigue warning device of the present invention.
Figure 10:
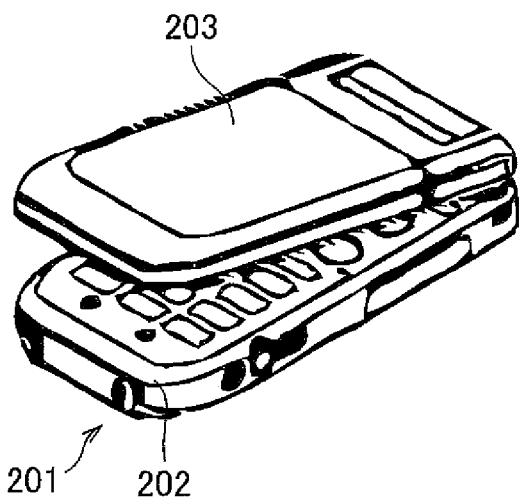
Figure 10:
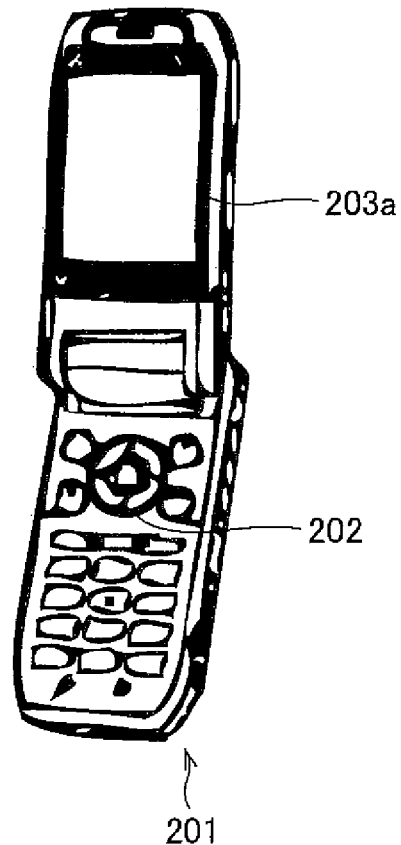

FIGS. 10 (*a*) through 10 (*c*) are drawings showing examples of an appearance of a mobile phone including the fatigue warning device explained by using FIG. 1. Hereinafter, this mobile phone is referred to as "mobile phone including the present invention product" and the whole electronic apparatuses having the function of the present invention are referred to as "present invention product". Except description of the mobile phone, description of the mobile phone including the present invention product relates to an arrangement of the present invention product.

As shown in FIG. 10 (*a*), a mobile phone including the present invention product 201 is a foldable mobile phone and is constituted by a body 202 and a lid body 203. The mobile phone including the present invention product is different from a normal mobile phone only in that the fatigue estimation device 1 and the fatigue warning device 10 of the present embodiment are mounted.

As shown in FIG. 10 (*c*), keys for operation of a mobile phone are arranged on the body 202, and a display section 203*a* of the lid body 203 displays every kind of functions of a mobile phone.

When the mobile phone including the present invention product 201 is not used, a user normally folds the mobile phone including the present invention product 201 as shown in FIG. 10 (a) and put it into a trouser pocket or the like. When the user uses the mobile phone including the present invention product 201, the mobile phone including the present invention product 201 is opened from a state of FIG. 10 (a) via a state of FIG. 10 (b) to a state of FIG. 10 (c).

In the mobile phone including the present invention product 201, it is possible to issue a fatigue warning to a user through screen display of the display section 203a. The user can confirm this fatigue warning with the same action as receiving a call and receiving/transmitting a mail. That is, the user can confirm his fatigue level by opening the mobile phone including the present invention product 201 from a state of FIG. 10 (a) via a state of FIG. 10 (b) to a state of FIG. 10 (c) and looking at screen display on the display section 203a.

The above method is not the only method for issuing a fatigue warning by using the mobile phone including the present invention product 201. For example, if the lid body 203 includes a small display section, the small display section can display a fatigue state. This makes it possible to confirm a fatigue state without opening the mobile phone including the present invention product 201. However, the display section 203a can display a fatigue state more detailedly on a larger screen than the small display section, and therefore can deliver a more accurate fatigue state to a user.

Further, it is needless to say that a fatigue state can be provided to a user not only by the screen display on the display section 203a but also by various methods such as sound, vibration or by a combination thereof.

For example, when a fatigue level of 70% is detected, the display section 203a can display a message encouraging a user to take a rest with a short beep. When a fatigue level of 90% or higher is detected, a fatigue warning may be continuously issued by using a beep or vibration until confirmation of a message by a user is detected. For example, the confirmation of a message by a user can be detected by detecting that the lid body 203 is opened from a folded state of the mobile phone including the present invention product 201. This makes it possible to surely convey a fatigue warning to a user.

Figure 11:
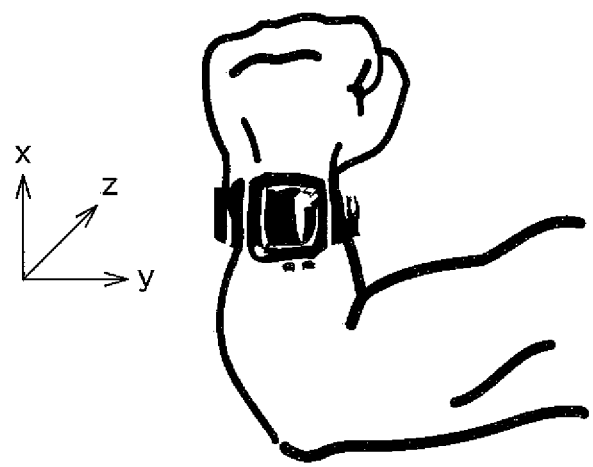
FIG. 11 (a) is a drawing showing a state in which a person is wearing a wristwatch including a body motion detection section of FIG. 1 on his wrist.
Figure 11:
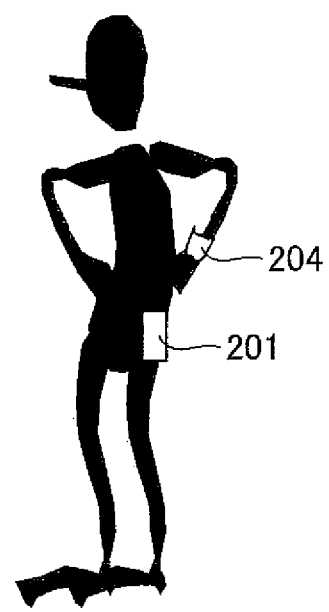

FIG. 11 (a) is a drawing showing a state in which a person is wearing a wristwatch including the body motion detection section 2 of FIG. 1 on his wrist.

The wristwatch including the body motion detection section 2 does not differ from a normal wristwatch in appearance and can show the time. However, the wristwatch including the body motion detection section 2 is different from a normal wristwatch in that the acceleration sensor 4, the first data storage section 5 and the data transmitting section 6 which are shown in FIG. 1 are provided in the wristwatch including the body motion detection section 2.

FIG. 11 (b) is a drawing showing an image of the present invention product being used in a usual manner. As shown in FIG. 11 (b), when the present invention product is used, a user always carries the mobile phone including the present invention product 201 in a trouser pocket or the like and wears a wristwatch 204 including the body motion detection section 2 on his wrist.

Basically, because the mobile phone including the present invention product 201 and the wristwatch 204 frequently communicate with each other, the two must be within a range where the two can communicate with each other. However, the body motion detection section 2 includes the first data storage section 5. Therefore, while the first data storage section 5 can store an acceleration data, it is possible to acquire user's acceleration data without interruption even if communication between the mobile phone including the present invention product 201 and the wristwatch 204 is interrupted.

FIG. 11 (b) shows an arrangement in which the mobile phone including the present invention product 201 and the wristwatch 204 are separated from each other. It should be noted that these two may not be separated from each other. For example, if a user always carries a mobile phone including an acceleration sensor, a function of the fatigue warning device of the present invention can be realized only by the mobile phone, and the number of parts can be decreased. However, in the present embodiment, the arrangement in which the mobile phone including the present invention product 201 and the wristwatch 204 are separated from each other is adopted because a user's fatigue level can be most accurately estimated by using an acceleration of the wrist.

[6. Warning Process]

Figure 12:
FIG. 12 (a) is a drawing showing a warning message displayed on a mobile phone including a fatigue warning device of the present invention.

For example, when the fatigue warning determining section 11 judges that a fatigue level estimated by the fatigue level estimation section 9 is 70% or higher, a mobile phone including the present invention product issues the sound of a beep and displays, on the display section 203a, a message encouraging a user to take a rest, as shown in FIG. 12 (a).

It is possible to set a plurality of fatigue warning levels. For example, when the fatigue warning determining section 11 judges that a fatigue level estimated by the fatigue level estimation section 9 is 90% or higher, a message with higher urgency may be displayed.

A person cannot recover from fatigue so easily even if a rest is taken. Therefore, it is preferable that a fatigue level is estimated at 30 minutes intervals, and a fatigue warning which was displayed once is not displayed for next two hours. This makes it unnecessary for a user to confirm a fatigue warning over and over again.

Further, a fatigue warning does not always require urgency. For example, as shown in FIG. 12 (c), by displaying a message indirectly recommending a user to take a rest in accordance with a fatigue level before the closing time, the user can calmly decide subsequent actions based on the message.

Further, as shown in FIG. 12 (d), by displaying, on the display section 203a, a graph showing the temporal transition of a fatigue level, a user can confirm the temporal transition of his fatigue level.

Further, those who the result of fatigue estimation is conveyed are not limited to those who wear the present invention product. Further, the present invention product does not necessarily need to be mounted in a mobile phone and may be mounted in other apparatuses. The following explains an embodiment in which the result of fatigue estimation is conveyed to those who do not wear the present invention product.

An embodiment where a wearer of the present invention product is an athlete, and the result of fatigue estimation is delivered to a manager of the athlete is explained with reference to FIG. 12 (e). As shown in FIG. 12 (e), by displaying a message telling that the athlete is in a fatigue state, the manager can call for the change at an appropriate timing without directly asking whether the athlete is in a fatigue state or not and without trusting his intuition and experience.

When the result of fatigue estimation is delivered to the manager, the fatigue presenting section 12 is not limited to a display section of a mobile phone. That is, it is only required that the fatigue presenting section 12 is mounted on an electronic apparatus having a notification function, and the result of fatigue estimation is delivered to the manager by using the fatigue presenting section 12. Further, the present invention product is used in a stadium and therefore is vulnerable to water and dust. Therefore, there is a case in which it is inappropriate to mount the fatigue presenting section 12 in an electronic apparatus. In this case, the result of fatigue estimation may be delivered by using voice.

Further, the result of fatigue estimation can be conveyed to those who do not wear the present invention product, for example, by providing, in the present invention product, transmitting means (not shown) for transmitting fatigue level information via network to the outside, the fatigue level information concerning the result of estimation of a fatigue level. The transmitting means is explained later.

For example, as shown in FIG. 12 (f), it is possible to display, on the display section 203a, a message telling that the result of fatigue estimation which the fatigue warning determining section 11 judged is delivered to a medical agency. By instantly transmitting, to a medical agency, fatigue level information concerning the result of estimation of a fatigue level, it is possible to deal with user's fatigue and reduce user's burden before a serious situation is caused.

Further, an electronic apparatus having the functions of the present invention is not limited to a mobile phone and may be a personal computer or an on-board apparatus. If a personal computer having the function of estimating a fatigue level is used in business, the personal computer can judge whether a user is feeling fatigue or not during work. If judged that the user is feeling fatigue, the fatigue presenting section 12 provided in the personal computer can recommend for the user to take a rest, and overwork can be prevented. Further, if an on-board apparatus has a function of estimating a fatigue level, the fatigue presenting section 12 provided on the on-board apparatus can inform a user of too much driving and timing of a rest, and accidents can be prevented.

Further, it is unnecessary to conduct estimation of a fatigue level using the present invention product in real time. For example, when a data concerning the result of fatigue level estimation is stored for a certain period, a fatigue level can be estimated from the stored data by using a home personal computer. This makes it possible to understand a transition of a fatigue level for a past certain period afterward.

Further, it is desirable that processing steps can be added to a program for executing the flow chart for estimating a fatigue level in order to realize more accurate fatigue level estimation in the future. Especially, when a mobile phone as shown in the present embodiment is used, it is possible to easily download a program from a server by a communication function which is an original function of a mobile phone and to update a program for fatigue level estimation. Therefore, such a mobile phone is suitable to add processing steps afterward.

Fatigue is a common symptom of a nervous system disease such as depression and chronic fatigue syndrome. Further, in recent years, accidents from fatigue and diseases from overworking have become subjects of discussion. Therefore, if fatigue can be easily detected at any time, it is possible to detect such a nervous system disease at an early stage and severity of a symptom, and it is possible to prevent accidents from fatigue. Therefore, it is very meaningful.

In the above embodiment, a fatigue level is calculated at a mobile phone side. However, because the calculation of a fatigue level includes complicated calculation, there is a case in which too much loads are added to a mobile phone. Therefore, another arrangement is possible in which body motion data is obtained and stored at a mobile phone, the obtained body motion data is transmitted to a predetermined server, and a fatigue level is calculated at the server or a workstation connected to the server. Further, by transmitting the calculated fatigue level to a user's mobile phone, the fatigue level may be displayed on the mobile phone, and a fatigue warning may be issued from the mobile phone. Further, the fatigue level calculated at the server may be transmitted to a medical agency, a manager of the user, relatives and friends of the user in addition to the user.

[7. Supplement]

Furthermore, the fatigue estimation method carried out by the fatigue estimation device of the present invention can be recorded, as a fatigue estimation program, in a computer-readable storage medium recording programs executed in a computer. This makes it possible to provide a portable storage medium containing the program for carrying out the fatigue estimation method of the present invention.

The storage medium may be a memory (not shown), for example, a program medium such as a ROM because a microcomputer executes processing, or may be a program medium which can be read by inserting the storage medium into a program reading device provided as an external storage device (not shown).

In each case, an arrangement in which a microprocessor accesses and executes the contained program is possible. Alternately, another arrangement is possible in which the program is executed by reading out the program and downloading the read program to a program storage area (not shown) of a microcomputer. In this case, a program for downloading is stored in a body device in advance.

The program medium is a storage medium which can be separated from a body device and may be a medium fixedly containing programs, for example, a tape, such as a magnetic tape or a cassette tape; a magnetic disk, such as a floppy (Registered Trademark) disk or a hard disk, or an optical disk, such as CD-ROM/MO/MD/DVD; a card, such as an IC card (memory card) or an optical card; or a semiconductor memory, such as a mask ROM/EPROM (Erasable Programmable Read Only Memory)/EEPROM (Electrically Erasable Programmable Read Only Memory)/flash ROM.

Further, in this case, a system is configured such that connection to a communication network including Internet is possible. Therefore, the program medium may be a medium for fluidly containing programs by downloading programs from the communication network. When a program is downloaded from the communication network, the program for download may be stored in a receiving apparatus in advance or may be installed from another storage medium.

As described above, a fatigue estimation device of the present invention includes activity level detection means for continuously detecting the frequency of a user's activity as an activity level and outputs, to fatigue level estimation means, the activity level detected by the activity level detection means, the fatigue level estimation means estimating a user's fatigue level on the basis of the activity level.

As a result of diligent studies, the inventors of the present invention found out that when a person is feeling fatigue, there is a certain tendency in the activity level. According to the fatigue estimation device of the present invention, a user's activity level can be automatically detected by the activity level detection means. Further, the fatigue level estimation means estimates the user's fatigue level on the basis of the activity level. Therefore, according to the fatigue level estimation means, the fatigue level can be automatically estimated on the basis of the activity level automatically detected by the activity level detection means.

As describe above, in the fatigue estimation device of the present invention, a user's activity level is automatically detected by the activity level detection means, and a fatigue level is automatically detected by the fatigue level estimation means on the basis of the detected activity level. Therefore, it is possible to easily estimate a user's fatigue level.

Further, only the activity level detection means and the fatigue level estimation means are required for the estimation of a user's fatigue level. Therefore, a user's fatigue level can be estimated at a low cost.

In the fatigue estimation device having the above arrangement, it is preferable that the fatigue level estimation means estimates a fatigue level by detecting a whether or not there is tendency that an activity level which is constantly high becomes low for a shorter time than a time period in which the high activity level is detected.

That is, when a person is feeling fatigue, there is a remarkable tendency that a continuously high activity level becomes low for a shorter time than a time period in which the high activity level is detected. The fatigue level estimation means estimates a fatigue level by detecting this tendency. Therefore, a user's fatigue can be accurately detected, and a user's fatigue level can be accurately estimated.

Further, it is preferable that the fatigue level estimation means detects the tendency of the activity level by statistically analyzing the activity level.

Specifically, the tendency of the activity level in a fatigue state can be accurately detected by statistically analyzing the activity level, for example, by calculating the skewness and the average of the activity level. Therefore, a user's fatigue level can be more accurately estimated by statistically analyzing the activity level.

Further, it is preferable that the fatigue level estimation means detects the tendency of the activity level after a long-term fluctuation component is removed from the activity level.

That is, when the long-term fluctuation component is removed, an activity level of a normal person who is feeling fatigue and an activity level of a patient with chronic fatigue syndrome have a similar tendency. Therefore, in the above arrangement, the fatigue level estimation means detects the tendency of the activity level after a long-term fluctuation component is removed from the activity level. This makes it possible to detect fatigue of a patient with chronic fatigue syndrome.

The fatigue level estimation means can remove the long-term fluctuation component of the activity level by differentiating the activity level with respect to time. Alternately, the long-term fluctuation component of the activity level can be removed by obtaining difference values of the activity level over time. Alternately, a regression curve of the activity level may be removed from the activity level as the long-term fluctuation component of the activity level.

Further, it is preferable that the fatigue level estimation means corrects an allowable range of the fatigue level to a predetermined range.

According to the above arrangement, the allowable range of an estimated fatigue level is corrected to the predetermined range by the fatigue level estimation means. Therefore, when the predetermined range obtained by correcting the allowable range matches with an allowable range of a value obtained by quantifying a fatigue level a user actually feels, the value of the estimated fatigue level can be more appropriate.

Further, it is preferable that the fatigue level estimation means corrects the allowable range of the fatigue level to the predetermined range by using a function for changing an output value in response to a change of an input value in such a manner that the output value is changed with a higher sensitivity for an input value in a vicinity of a specific value, than for an input value which is not in a vicinity of the specific value.

According to the above arrangement, when the specific value is a value where a clear understanding of a change of a fatigue level is desired and the input value is the estimated fatigue level itself, the output value of this function greatly changes in response to a change in the vicinity of the value where a clear understanding of a change of a fatigue level is desired. Therefore, a fatigue level can be more accurately detected by obtaining the output value of the function.

Examples of such a function include the sigmoid function.

Further, it is preferable that the activity level detection means detects the activity level on the basis of acceleration of movements of a user's entire body or a part of the body.

That is, when a user is in a fatigue state, movements of the user's body decrease. Therefore, by detecting acceleration of movements of the user's entire body or a part of the body, it is possible to detect the decrease of movements in a fatigue state, and it is possible to more accurately estimate a fatigue level.

Furthermore, it is preferable that the activity level detection means detects the activity level as the number of times the acceleration changes.

Further, it is preferable that the activity level detection means detects the number of times the acceleration changes as the number of times the acceleration passes the predetermined threshold.

Specifically, when the number of times the acceleration changes is detected by using the number of times the acceleration passes the predetermined threshold, the number of times the acceleration changes can be detected with a small amount of data. This makes it possible to efficiently detect a user's activity level and estimate the fatigue level.

Furthermore, the activity level detection means may detect the acceleration on the basis of a temporal change in positional information of a user's whole body or a part of the body.

Furthermore, the acceleration may be three-dimensional acceleration of movements of a user's entire body or a part of the body.

According to the above arrangement, it is possible to obtain more accurate acceleration. Therefore, a fatigue level can be more accurately estimated.

Further, the acceleration may be acceleration of movements of a user's entire body or a part of the body in a one-dimensional direction.

When an activity level is detected on the basis of acceleration of user's movements in a one-dimensional direction, it is possible to reduce the amount of data concerning the activity level. This makes it possible to efficiently detect a user's activity level and estimate the fatigue level.

The "movements in a one-dimensional direction" means user's movements in a direction of one axis among x, y and z-axes in a case where user's movements are defined in three axes direction of x, y and z-axes. A one-axis output acceleration sensor is sufficient to evaluate movements in a one-dimensional direction.

Further, it is preferable that the acceleration is acceleration of movements of a user's wrist.

That is, the tendency that movements decrease in a fatigue state appears remarkably at the wrist. Therefore, by detecting the acceleration of movements of the user's wrist, it is possible to accurately detect an activity level and more accurately estimate a fatigue level.

Furthermore, it is preferable that the activity level detection means is provided in a wristwatch.

That is, because a wristwatch is normally attached to the wrist, when the activity level detection means is provided in a wristwatch, acceleration of the wrist can be accurately detected. This makes it possible to accurately detect an activity level and more accurately estimate a fatigue level.

Further, the activity level detection means may detect the activity level on the basis of positional information of a user's entire body or a part of the body.

That is, the tendency that movements of a user's body decrease in a fatigue state can be detected from user's positional information. That is, when movements of a user's body decrease, a change of a user's position decreases accordingly. Therefore, by detecting the tendency that the change of the user's position decreases on the basis of the positional information, it is possible to detect user's fatigue.

Further, according to the positional information, a user's position can be detected in addition to a user's fatigue level.

Further, the activity level detection means may detect the activity level on the basis of image information of a user's entire body or a part of the body.

Specifically, image information of a user's entire body or a part of the body can be obtained without restricting movements of the user by using image pickup means such as a video camera. This makes it possible to estimate a fatigue level without discomforting a user.

Furthermore, it is preferable that actual fatigue level information obtained by asking a user about his condition corresponds to estimated fatigue level information estimated by the fatigue level estimation means.

Specifically, the actual fatigue level information obtained by asking a user about his condition is most reliable information about user's fatigue. Therefore, when the actual fatigue level information corresponds to the estimated fatigue level information estimated by the fatigue level estimation means, it is possible to more accurately detect a user's fatigue level and take appropriate actions.

Furthermore, it is preferable that the fatigue level estimation means is provided in a server separated from the fatigue estimation device.

Specifically, when the fatigue level estimation means estimates a user's fatigue level on the basis of an activity level in the server, the fatigue estimation device itself can be made more compact.

Further, it is possible to send another person the fatigue level estimated in the server. Therefore, even if a user himself cannot deal with his fatigue, someone who received the fatigue level can take measures against the fatigue.

Further, a fatigue warning device of the present invention includes a fatigue estimation device having the above arrangement, fatigue warning determining means for determining a degree of a fatigue level estimated by the fatigue level estimation means and determining whether to issue a warning concerning user's fatigue, and fatigue presenting means for presenting a fatigue warning on the basis of the determination.

According to the above arrangement, the fatigue warning determining means determines whether to issue a warning concerning user's fatigue, and the fatigue presenting means presents a fatigue warning on the basis of the determination.

Therefore, a user and others can easily understand a user's fatigue level by looking at a fatigue warning presented by the fatigue presenting means. This makes it possible to avoid troubles caused by fatigue.

Further, the fatigue presenting means is characterized by presenting the warning at predetermined intervals.

Specifically, a user cannot recover from fatigue until a certain amount of time passes even if the user takes measures against fatigue. Therefore, even if a user who is not recovering from fatigue receives a fatigue warning from the fatigue presenting means, the warning can be annoying for the user.

Therefore, when time which takes for a user to recover from fatigue is set to be the predetermined interval, and the fatigue presenting means presents a fatigue warning at the predetermined interval, it is possible to reduce the annoyance of the user.

Furthermore, the fatigue presenting means may present the warning to someone who is not a user whose fatigue level is estimated by the fatigue level estimation means.

According to the above arrangement, even if a user himself cannot deal with his fatigue, someone who confirmed a fatigue warning presented by the fatigue presenting means can take measures against the fatigue.

Further, an electronic apparatus of the present invention includes a fatigue estimation device having the above arrangement or a fatigue warning device having the above arrangement.

When the fatigue estimation device having the above arrangement or the fatigue warning device having the above arrangement is provided in the electronic device, it is possible to estimate a fatigue level without feeling discomfort in daily life.

Further, it is preferable that the electronic apparatus includes transmitting means for transmitting, to the outside, estimated fatigue level information concerning a fatigue level estimated by the fatigue level estimation means.

According to the above arrangement, the estimated fatigue level information is transmitted to the outside. This makes it possible to confirm a user's fatigue level at a destination of the estimated fatigue level information. Therefore, even if a user himself cannot deal with his fatigue, someone who confirmed the information at the destination of the information can take measures against the fatigue.

Further, it is preferable that the electronic apparatus is a mobile phone. Normally, a user always carries a mobile phone. Therefore, when activity level detection means is provided in the mobile phone, an activity level can be accurately detected.

In order to solve the above problems, a fatigue estimation method of the present invention includes detecting an activity level by continuously detecting a frequency of a user's activity as the activity level by using activity level detection means provided in a fatigue estimation device, and outputting the activity level detected at the activity level detection step, to fatigue level estimation means for estimating a user's fatigue level. According to the fatigue estimation method, it is possible to obtain the same effect as the fatigue estimation means of the present invention.

Further, in order to solve the above problems, a fatigue estimation program of the present invention is a fatigue estimation program for executing the fatigue estimation method of the present invention and causing a computer to execute the steps.

By installing the fatigue estimation program of the present invention, it is possible to use any computer in estimating a fatigue level.

Furthermore, by storing the fatigue estimation program in a computer-readable storage medium, it is possible to execute the fatigue estimation program in any computer.

The fatigue estimation device of the present invention may be arranged so as to continuously detect a user's activity state and detect fatigue based on the detected activity state.

In a fatigue estimation device having the above arrangement, it is preferable that fatigue is detected based on a relatively low activity state in a continuous activity state. Further, it is preferable that the relatively low activity state is obtained by removing a long-term fluctuation component from the continuous activity state.

Furthermore, the relatively low activity state may be obtained by statistically analyzing the detected activity state.

The long-term fluctuation component can be removed by obtaining differential values or difference values of the activity state.

Further, it is preferable that a regression curve is used as the long-term fluctuation component.

Furthermore, it is preferable that a process of confining a calculated fatigue level within a predetermined range is carried out. When a process of confining a calculated fatigue level within a predetermined range is carried out, it is preferable that the sensitivity is high in the vicinity of a specific value.

Further, it is preferable that the activity state is obtained from acceleration of an entire body or a part of the body. The activity sate may be obtained from positional information of an entire body or a part of the body or may be obtained from image information of an entire body or a part of the body.

Furthermore, it is preferable that the activity state is obtained based on a change of the acceleration. Further, the acceleration may be obtained based on the positional information.

Furthermore, the change of the acceleration may be obtained by counting the number of times the acceleration intersects with a predetermined value.

Further, it is preferable that the activity state is obtained from a wrist as the part of the body. Further, it is preferable that the acceleration is one-dimensional acceleration.

Furthermore, when a predetermined fatigue is detected, it is preferable that a notice is given to a user. It is preferable that this notice is given at a predetermined timing. Further, when a predetermined fatigue is detected, it is preferable that a notice is given to another user who is not a user whose fatigue is detected.

Further, an electronic apparatus of the present invention may include a fatigue estimation device having the above arrangement. It is preferable that this electronic apparatus has a communication function, and it is more preferable that this electronic apparatus is a mobile phone. Furthermore, it is preferable that a fatigue estimation program can be added afterward. It is preferable that a state estimation device of the present invention is a wristwatch having a function of acquiring an activity state of a wrist.

Industrial Applicability

According to the present invention, it is possible to easily estimate a fatigue level with a low cost. In recent years, various symptoms caused by fatigue and accidents caused by fatigue have become an issue. However, according to the present invention, it is possible to find such symptoms in an early stage and to prevent such accidents.

The invention claimed is:

1. A fatigue estimation device comprising:
an activity level detector configured to continuously detect a user's movement from a user's body motion and to quantify body motion of a user as an activity level,
the fatigue estimation device configured to output, to a fatigue level estimator, the activity level detected by the activity level detector, the fatigue level estimator configured to estimate a user's fatigue level based on the activity level, and wherein
the fatigue level estimator is configured to estimate a fatigue level by detecting whether or not there is a tendency that a continuously high activity level becomes low for several tens of seconds corresponding to a time period during which the user stops the user's movement regardless of the user's will to continue the movement and
wherein the fatigue level estimator is configured to detect the tendency of the activity level by a combination of statistical analyses of the activity level, the combination including skewness and average of the quantified body motion,
wherein the skewness is the amount of asymmetry about the average.

2. The fatigue estimation device according to claim 1, wherein the fatigue level estimator is configured to detect the tendency of the activity level after a long-term fluctuation component is removed from the activity level.

3. A fatigue estimation device comprising:
an activity level detector configured to continuously quantify a frequency of a user's activity as an activity level,
the fatigue estimation device configured to output the activity level quantified by the activity level detector to a fatigue level estimator, the fatigue level estimator configured to estimate a fatigue level by (i) removing a long-term fluctuation component from the activity level by differentiating the activity level with respect to time and (ii) detecting whether or not there is a tendency that an continuously high activity level becomes low for a shorter time than a time period in which the high activity level is detected, the shorter time corresponding to a time period during which the user stops the user's movement regardless of the user's will to continue the movement and
wherein the fatigue level estimator is configured to detect the tendency of the activity level by a combination of statistical analyses of the activity level, the combination including skewness and average of the quantified frequency of a user's activity,
wherein the skewness is the amount of asymmetry about the average.

4. The fatigue estimation device according to claim 1, wherein the fatigue level estimator is configured to remove a long-term fluctuation component from the activity level by obtaining difference values of the activity level over time.

5. A fatigue estimation device comprising:
an activity level detector configured to continuously quantify a frequency of a user's activity as an activity level,
the fatigue estimation device configured to output the activity level detected by the activity level detection section to a fatigue level estimator, the fatigue level estimator configured to estimate a fatigue level by (i) obtaining a regression curve of the activity level, (ii) removing the regression curve from the activity level as a long-term fluctuation component of the activity level, and (iii) detecting whether or not there is a tendency of the activity level that a continuously high activity level becomes low for a shorter time than a time period in which the high activity level is detected, the shorter time corresponding to a time period during which the user stops the user's movement regardless of the user's will to continue the movement and
wherein the fatigue level estimator is configured to detect the tendency of the activity level by a combination of statistical analyses of the activity level, the combination including skewness and average of the quantified frequency of a user's activity,
wherein the skewness is the amount of asymmetry about the quantified frequency of a user's activity.

6. A fatigue estimation device comprising:
an activity level detector configured to continuously detect a frequency of a user's activity as an activity level,
the fatigue estimation device configured to output, to a fatigue level estimator, the activity level detected by the activity level detection section, the fatigue level estimator configured to estimate a user's fatigue level on a basis of the activity level and to correct an allowable range of the fatigue level to a predetermined range,
wherein the fatigue level estimator is configured to correct the allowable range of the fatigue level to the predetermined range by using a sigmoid function for changing an output value in response to a change of an input value in such a manner that the output value is changed with a higher sensitivity for an input value in a vicinity of a specific value, than for an input value which is not in a vicinity of the specific value.

7. The fatigue estimation device according claim 1, wherein the activity level detector is configured to detect the activity level on a basis of acceleration of movements of a user's entire body or a part of the body.

8. A fatigue estimation device comprising:
an activity level detector configured to continuously detect, as an activity level which is a frequency of a user's activity, a number of times acceleration of movements of a user's entire body or a part of the body changes, the fatigue estimation device configured to output, to a fatigue level estimator, the activity level detected by the activity level detector, the fatigue level estimator configured to estimate a user's fatigue level on a basis of the activity level,
the fatigue level estimator providing a plurality of thresholds, and estimating, for each of the thresholds, the user's fatigue level based on a combination of statistical analyses of an elapsed time between a time when the acceleration changes from a value higher than the threshold to a value lower than the threshold and a time when the acceleration changes from a value lower than the threshold to a value higher than the threshold,
the statistical analyses being made with the use of at least skewness.

9. The fatigue estimation device according to claim 8, wherein the activity level detector is configured to detect the number of times the acceleration changes as a number of times the acceleration passes a predetermined threshold.

10. The fatigue estimation device according to claim 7, wherein the activity level detector is configured to detect the activity level on a basis of a temporal change in positional information of the user's entire body or the part of the body.

11. The fatigue estimation device according to claim 7, wherein the acceleration is three-dimensional acceleration of movements of the user's entire body or the part of the body.

12. The fatigue estimation device according to claim 7, wherein the acceleration is one-dimensional acceleration of movements of the user's entire body or the part of the body.

13. The fatigue estimation device according to claim 7, wherein the acceleration is acceleration of movements of a user's wrist.

14. The fatigue estimation device according to claim 13, wherein the activity level detector is provided in a wristwatch.

15. The fatigue estimation device according to claim 1, wherein the activity level detector is configured to detect the activity level on a basis of positional information of a user's entire body or a part of the body.

16. The fatigue estimation device according to claim 1, wherein the activity level detector is configured to detect the activity level on a basis of image information of a user's entire body or a part of the body.

17. The fatigue estimation device according to claim 1, wherein the fatigue level estimator is provided in a server separated from the fatigue estimation device.

18. A fatigue warning device comprising:
a fatigue estimation device comprising,
an activity level detector configured to continuously detect a user's movement from a user's body motion and to quantify body motion of a user as an activity level,
the fatigue estimation device configured to output, to a fatigue level estimator, the activity level detected by the activity level detector, the fatigue level estimator configured to estimate a user's fatigue level based on the activity level, wherein the fatigue level estimator is configured to estimate a fatigue level by detecting whether or not there is a tendency that a continuously high activity level becomes low for several tens of seconds corresponding to a time period during which the user stops the user's movement regardless of the user's will to continue the movement and wherein the fatigue level estimator is configured to detect the tendency of the activity level by a combination of statistical analyses of the activity level, the combination including skewness and average of the quantified body motion, wherein the skewness is the amount of asymmetry about the average;
a fatigue warning processor configured to determine a degree of a fatigue level estimated by the fatigue level estimation section and to determine whether to issue a warning concerning user's fatigue, and
a fatigue presentation device configured to present the warning on the basis of the determination of the fatigue warning processor.

19. The fatigue warning device according to claim 18, wherein the fatigue presentation device is configured to present the warning at predetermined intervals.

20. The fatigue warning device according to claim 18, wherein the fatigue presentation device is configured to present the warning to someone who is not a person whose fatigue level is estimated by the fatigue level estimation section.

21. An electronic apparatus comprising:
a fatigue estimation device comprising,
an activity level detector configured to continuously detect a user's movement from a user's body motion and to quantify body motion of a user as an activity level,
the fatigue estimation device configured to output, to a fatigue level estimator, the activity level detected by the activity level detector, the fatigue level estimator configured to estimate a user's fatigue level based on the activity level, wherein the fatigue level estimator is configured to estimate a fatigue level by detecting whether or not there is a tendency that a continuously high activity level becomes low for several tens of seconds corresponding to a time period during which the user stops the user's movement regardless of the user's will to continue the movement, wherein the fatigue level estimator is configured to detect the tendency of the activity level by a combination of statistical analyses of the activity level, the combination including skewness and average of the quantified body motion, wherein the skewness is the amount of asymmetry about the average; and
a fatigue warning device.

22. The electronic apparatus according to claim 21, further comprising:
a transmitter configured to transmit, to an outside device, estimated fatigue level information concerning the fatigue level estimated by the fatigue level estimation section.

23. The electronic apparatus according to claim 21, wherein the electronic apparatus is a mobile phone.

24. A fatigue estimation method comprising:
- detecting an activity level by continuously detecting a frequency of a user's activity by quantifying body motion of a user as the activity level by using an activity level detector provided in a fatigue estimation device, and
- outputting the activity level detected at the activity level detection step, to a fatigue level estimator for estimating a user's fatigue level based on an activity level, and wherein
- the fatigue level estimator estimates a fatigue level by detecting whether or not there is a tendency that a continuously high activity level becomes low for several tens of seconds corresponding to a time period during which the user stops the user's movement regardless of the user's will to continue the movement, wherein the fatigue level estimator is configured to detect the tendency of the activity level by a combination of statistical analyses of the activity level, the combination including skewness and average of the quantified body motion,
- wherein the skewness is the amount of asymmetry about the average.

25. A non-transitory tangible computer-readable medium storing computer-implementable instructions that when executed by a processor execute a fatigue estimation method, the method comprising:
- detecting an activity level by continuously detecting a frequency of a user's activity by quantifying body motion of a user as the activity level by using an activity level detector provided in a fatigue estimation device, and
- outputting the activity level detected at the activity level detection step, to a fatigue level estimator for estimating a user's fatigue level based on an activity level, and wherein
- the fatigue level estimator estimates a fatigue level by detecting whether or not there is a tendency that a continuously high activity level becomes low for several tens of seconds corresponding to a time period during which the user stops the user's movement regardless of the user's will to continue the movement, wherein the fatigue level estimator is configured to detect the tendency of the activity level by a combination of statistical analyses of the activity level, the combination including skewness and average of the quantified body motion,
- wherein the skewness is the amount of asymmetry about the average.

26. The fatigue estimation device of claim 1, wherein the fatigue estimation device is configured to make actual fatigue level information obtained by asking a user about his condition correspond to estimated fatigue level information estimated by the fatigue level estimator.

27. The fatigue estimation device of claim 3, wherein the fatigue estimation device is configured to make actual fatigue level information obtained by asking a user about his condition correspond to estimated fatigue level information estimated by the fatigue level estimator.

28. The fatigue estimation device of claim 5, wherein the fatigue estimation device is configured to make actual fatigue level information obtained by asking a user about his condition correspond to estimated fatigue level information estimated by the fatigue level estimator.

29. The fatigue estimation device of claim 6, wherein the fatigue estimation device is configured to make actual fatigue level information obtained by asking a user about his condition correspond to estimated fatigue level information estimated by the fatigue level estimator.

30. The fatigue estimation device of claim 8, wherein the fatigue estimation device is configured to make actual fatigue level information obtained by asking a user about his condition correspond to estimated fatigue level infoiniation estimated by the fatigue level estimator.

31. The fatigue estimation device of claim 1, wherein:
- the fatigue level estimator is configured to obtain a regression curve of the activity level and to remove the regression curve from the activity level as a long-term fluctuation component of the activity level; and
- the fatigue level estimator is configured to correct the allowable range of the fatigue level to a predetermined range by using a function for changing an output value in response to a change of an input value in such a manner that the output value is changed with a higher sensitivity for an input value in a vicinity of a specific value, than for an input value which is not in the vicinity of the specific value.

32. The fatigue estimation device of claim 3, wherein the fatigue level estimator is configured to correct the allowable range of the fatigue level to a predetermined range by using a function for changing an output value in response to a change of an input value in such a manner that the output value is changed with a higher sensitivity for an input value in a vicinity of a specific value, than for an input value which is not in the vicinity of the specific value.

33. The fatigue estimation device of claim 5, wherein the fatigue level estimator is configured to correct the allowable range of the fatigue level to a predetermined range by using a function for changing an output value in response to a change of an input value in such a manner that the output value is changed with a higher sensitivity for an input value in a vicinity of a specific value, than for an input value which is not in the vicinity of the specific value.

* * * * *